(12) United States Patent
Chan et al.

(10) Patent No.: US 7,402,396 B2
(45) Date of Patent: *Jul. 22, 2008

(54) CORE STRUCTURE OF GP41 FROM THE HIV ENVELOPE GLYCOPROTEIN

(75) Inventors: David C. Chan, Brookline, MA (US); Deborah Fass, Cambridge, MA (US); Min Lu, New York, NY (US); James M. Berger, Cambridge, MA (US); Peter S. Kim, Lexington, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 547 days.

This patent is subject to a terminal disclaimer.

(21) Appl. No.: 10/680,853

(22) Filed: Oct. 7, 2003

(65) Prior Publication Data

US 2005/0053917 A1 Mar. 10, 2005

Related U.S. Application Data

(60) Continuation of application No. 10/200,007, filed on Jul. 18, 2002, now abandoned, which is a continuation of application No. 09/484,925, filed on Jan. 18, 2000, now Pat. No. 6,506,554, which is a division of application No. 09/062,241, filed on Apr. 17, 1998, now Pat. No. 6,150,088.

(60) Provisional application No. 60/043,280, filed on Apr. 17, 1997.

(51) Int. Cl.
G01N 33/53 (2006.01)
(52) U.S. Cl. .......................................... 435/7.1; 435/5
(58) Field of Classification Search ..................... 435/5, 435/7.1
See application file for complete search history.

(56) References Cited

U.S. PATENT DOCUMENTS

| | | | |
|---|---|---|---|
| 5,444,044 A | 8/1995 | Jiang et al. |
| 5,464,933 A | 11/1995 | Bolognesi et al. |
| 5,656,480 A | 8/1997 | Wild et al. |
| 5,780,221 A | 7/1998 | Schumacher et al. |
| 5,840,843 A | 11/1998 | Jiang et al. |
| 6,150,088 A | 11/2000 | Chan et al. |
| 6,506,554 B1 | 1/2003 | Chan et al. |
| 6,747,126 B1 | 6/2004 | Eckert et al. |
| 6,818,740 B1 | 11/2004 | Eckert et al. |
| 6,841,657 B2 | 1/2005 | Eckert et al. |
| 7,053,179 B2 | 5/2006 | Root et al. |
| 7,226,598 B2 | 6/2007 | Eckert et al. |
| 2001/0047080 A1 | 11/2001 | Root et al. |
| 2002/0077284 A1 | 6/2002 | Eckert et al. |
| 2003/0082525 A1 | 5/2003 | Root et al. |
| 2003/0099935 A1 | 5/2003 | Chan et al. |
| 2004/0044183 A1 | 3/2004 | Eckert et al. |
| 2004/0213801 A1 | 10/2004 | Wild et al. |
| 2005/0221294 A1 | 10/2005 | Eckert et al. |
| 2006/0014139 A1 | 1/2006 | Root et al. |

FOREIGN PATENT DOCUMENTS

| | | |
|---|---|---|
| WO | WO 94/02505 | 2/1994 |
| WO | WO 96/40191 | 12/1996 |
| WO | WO 98/32848 A | 7/1998 |
| WO | WO 00/06599 | 2/2000 |
| WO | WO 00/40616 | 7/2000 |
| WO | WO 01/03723 A1 | 1/2001 |
| WO | WO 01/44286 A2 | 6/2001 |

OTHER PUBLICATIONS

Baum, Rudy, "Virus-cell Fusion Targeted for Drug Development," C&EN (1996).

Blacklow, Stephen C., et al., "A Trimeric Subdomain of the Simian Immunodeficiency Virus Envelope Glycoprotein," Biochemistry, 34(46):14955-14962 (1995).

Blake, James and Li, Choh Hao, "Adrenocorticotropin. 47. Synthesis and Biological Activity of Adrenocorticotropic Peptides Modified at the Tryptophan Position," J. Medicinal Chem. 18(4):423-426 (1975).

Borchardt, Allen et al., "Small Molecule-dependent genetic selection in stochastic nanodroplets as a means of detecting protein-ligand interactions on a large scale," Chem. & Biol. 4(12):961-968 (1997).

Bullough, Per A. et al., "Structure of influenza haemagglutinin at the pH of membrane fusion," Nature 371:37-43 (1994).

Caffrey, Michael et al., "Three-dimensional solution structure of the 44kDa ectodomain of SIV gp41," EMBO J. 17(16):4572-4584 (1998).

Cao, Jie et al., "Effects of Amino Acid Changes in the Extracellular Domain of the Human Immunodeficiency Virus Type 1 gp41 Envelope Glycoprotein," J. Virology 67(5):2747-2755 (1993).

Chabala, John C., "Solid-phase combinatorial chemistry and novel tagging methods for identifying leads," Curr. Opin. Biotech. 6:632-639 (1995).

Chakrabartty, Avijit et al.,"Aromatic Side-Chain Contribution to Far-Ultraviolet Circular Dichroism of Helical Peptides and Its Effect on Measurement of Helix Propensities," Biochemistry 32:5560-5565 (1993).

(Continued)

Primary Examiner—Bruce R. Campell
Assistant Examiner—Myron G. Hill
(74) Attorney, Agent, or Firm—Hamilton, Brook, Smith & Reynolds, P.C.

(57) ABSTRACT

Described are the crystal structure of the α-helical domain of the gp41 component of HIV-1 envelope glycoprotein which represents the core of fusion-active gp41, methods of identifying and designing drugs which inhibit gp41 function and drugs which do so.

3 Claims, 21 Drawing Sheets
(4 of 21 Drawing Sheet(s) Filed in Color)

OTHER PUBLICATIONS

Chambers, Philip, et al., "Heptad Repeat Sequences are Located Adjacent to Hydrophobic Regions in Several Types of Virus Fusion Glycoproteins," Journal of General Virology, 71:3075-3080 (1990).

Chan, David C., et al., "Evidence that a Prominent Cavity in the Coiled Coil of HIV Type I gp41 is an Attractive Drug Target," Proc. Natl. Acad. Sci. USA 95:15613-15617 (1998).

Chan, David C., et al., "Core Structure of gp41 from the HIV Envelope Glycoprotein," Cell 89:263-273 (1997).

Chan, David C. and Kim, Peter A., "HIV Entry and Its Inhibition," Cell 93:681-684 (1998).

Chen, Yee-Hsiung et al., "Determination of the Helix and Form of Proteins in Aqueous Solution by Circular Dichroism," Biochemistry 13(16):3350-3359 (1974).

Chen, Benjamin K. et al., "Distinct Modes of Human Immunodeficiency Virus Type 1 Proviral Latency Revealed by Superinfection of Nonproductively Infected Cell Lines with Recombinant Luciferase-Encoding Viruses," J. Virology 68(2):654-660 (1994).

Chen, Charlie L. et al., "One Bead-One Compound Combinatorial Peptide Library: Different Types of Screening," Methods in Enzymology 267:211-219 (1996).

Chen, Chin-Ho et al., "A Molecular Clasp in the Human Immunodeficiency Virus (HIV) Type 1 TM Protein Determines the Anti-HIV Activity of gp41 Derivatives:Implication for Viral Fusion," J. Virology 69(6):3771-3777 (1995).

Cole, James L. and Garsky, Victor M., "Thermodynamics of Peptide Inhibitor Binding to HIV-1 gp41," Biochemistry 40:5633-5641 (2001).

Delwart, Eric L., et al., "Retroviral Envelope Glycoproteins Contain a "Leucine Zipper"-like Repeat," AIDS Research and Human Retroviruses, 6(6):703-706 (1990).

Doering Don S. and Matsudaira, Paul, "Cysteine Scanning Mutagenesis at 40 of 76 Positions in Villin Headpiece Maps the F-Actin Binding Site and Structuring Features of the Domain," Biochemistry 35:12677-12685 (1996).

Dutch, Rebecca Ellis et al., "Paramyxovirus Fusion Protein: Characterization of the Core Trimer, a Rod-Shaper Complex with Helices in Anti-Parallel Orientation," Virology 254:147-159 (1999).

Eckert, Debra M., et al., "Inhibiting HIV-1 Entry: Discovery of D-Peptide Inhibitors that Target the gp41 Coiled-Coil Pocket," Cell 99:103-115 (1999).

Eckert, Debra M. et al., "Crystal Structure of GCN4-pIQI, a Trimeric Coiled Coil with Buried Polar Residues," J. Mol. Biol. 284:859-865 (1998).

Eckhart, Leopold et al., "Immunogenic Presentation of a Conserved gp41 Epitope of Human Immunodeficiency Virus Type I on Recombinant Surface Antigen of Hepatitis B Virus," J. Gen. Virol. 77:2001-2008 (1996).

Edelhoch, Harold, "Spectroscopic Determination of Trytophan and Tyrosine in Proteins," Biochemistry 6:(7):1948-1954 (1967).

Fass, Deborah et al., "Retrovirus envelop domain at 1.7 resolution," Nature Structural Biology 3(5):465-469 (1996).

Fass, Deborah and Kim, Peter S., "Dissection of a retrovirus envelope protein reveals structural similarity to influenza hemagglutinin," Current Biology 5(12):1-7(1995).

Furuta et al., "Capture of an early fusion-active conformation of HIV-1 gp41," Nature Structural Biology 5(4):276-279 (1998).

Gallaher, William R., et al., "A General Model for the Transmembrane Proteins of HIV and Other Retroviruses," Aids Research and Human Retroviruses, 5(4):431-440 (1989).

Harbury, Pehr B. et al., "Repacking protein cores with backbone freedom:Structure prediction for coiled coils," Proc. Natl. Acad. Sci, USA 92:8408-8412 (1995).

Harbury, Pehr B. et al., "Crystal structure of an isoleucine-zipper trimer," Nature 371:80-83 (1994).

Hirsch, Vanessa M. and Johnson, Philip R., "Pathogenic diversity of simian immunodeficiency viruses," Virus Research 32:183-206 (1994).

Hooft, Rob W.W. and Vriend, Gert, "Errors in protein structures," Nature 381:272 (1996).

Jiang, Shibo et al., "A conformation-Specific Monoclonal Antibody Reacting with Fusion-Active gp41 from the Human Immunodeficiency Virus Type 1 Envelope Glycoprotein," J. of Virology 72(12):10213-10217 (1998).

Jiang, S. et al., "A screening assay for antiviral compounds targeted to the HIV-1 gp41 core structure using a conformation-specific monoclonal antibody," J. Virol. Methods 80:85-96 (1999).

Jiang, Shibo et al., "HIV-1 inhibition by a peptide," Nature 365:113 (1993).

Jones, T.A. et al., "Improved Methods for Building Protein Models in Electron Density Maps and the Location of Errors in these Models," Acta Cryst. A47:110-119 (1991).

Judice, J. Kevin et al., "Inhibition of HIV type 1 infectivity by constrained -helical peptides:Implications for the viral fusion mechanism," Proc. Natl. Acad. Sci. USA 94:13426-13430 (1997).

Kilby, J. Michael et al., "Potent suppression of HIV-1 replication in humans by T-20, a peptide inhibitor of gp41-mediated virus entry," Nature Medicine 4(11):1302-1307 (1998).

Kliger, Yossef et al., "Mode of Action of an Antiviral Peptide from HIV-1," J. Biol. Chem. 276(2):1391-1397 (2001).

Kozarsky, Karen et al., "Glycosylation and Processing of the Human Immunodeficiency Virus Type 1 Envelope Protein," J. Acquired Immune Deficiency Syndromes 2:163-169 (1989).

Kubinyi, Hugo, "Combinatorial and computational approaches in structures-based drug design," Curr. Op. In Drug Disc. & Dev. 1(1):16-22 (1998).

Kuntz, Irwin D., "Structure-Based Strategies for Drug Design and Discovery," Science 257:1078-1082 (Aug. 1992).

La Casse, Rachel A. et al., "Fusion-Competent Vaccines: Broad Neutralization of Primary Isolates of HIV," Science 283:357-362 (1999).

Lam, Kit S. et al., "A new type of synthetic peptide library for identifying ligand-binding activity," Nature 354:82-84 (1991).

Lambert, D.M. et al., "Peptides from conserved regions of paramyxovirus fusion (F) proteins are potent inhibitors of viral fusion," Proc. Natl. Acad. Sci. USA 93:2186-2191 (1996).

Letvin, Norman L., "Progress in the Development of an HIV-1 Vaccine," Science 280:1875-1880 (1998).

Li, Zhe, et al., "Anti-malarial Drug Development Using Models of Enzyme Structure," Chemistry & Biology, 1:31-37 (1994).

Lu, Min, et al., "A Trimeric Structural Domain of the HIV-1 transmembrane glycoprotein," Nature Structural Biology, 2(12):1-8 (1995).

Lu, Min and Kim, Peter S., "A Trimeric Structural Subdomain of the HIV-1 Transmembrane Glycoprotein," J. Biomol. Structure & Dynamics 15(3):465-471 (1997).

Malashkevich, Vladimir N. et al., "Crystal structure of the simian immunodeficiency virus (SIV) gp41 core: Conserved helical interactions underlie the broad inhibitory activity of gp41 peptides," Proc. Natl. Acad. Sci. USA 95:9134-9139 (1998).

Meng, Elaine C., et al., "Automated Docking with Grid-Based Energy Evaluation," Journal of Computational Chemistry, 13(4):505-524 (1992).

Muster, Thomas et al., "Cross-Neutralizing Activity against Divergent human Immunodeficiency Virus Type 1 Isolates Induced by the gp41 Sequence ELDKWAS," J. Virology 68(6):4031-4034 (1994).

Muster, Thomas et al., "A Conserved Neutralizing Epitope on gp41 of Human Immunodeficiency Virus Type 1," J. Virology 67(11):6642-6647 (1993).

Nautiyal, Shivani and Alber, Tom, "Crystal structure of a designed, thermostable, heterotrimeric coiled coil," Protein Science 8:84-90 (1999).

Nolte, Alexis et al., "Mirror-design of L-oligonucleotide ligands binding to L-arginine," Nature Biotechnology 4:1116-1119 (1996).

O'Neil, Karyn T. and DeGrado, William F., "A Thermodynamic Scale for the Helix-Forming Tendencies of the Commonly Occurring Amino Acids," Science 250:646-351 (1990).

Purtscher, Martin et al., "Restricted antigenic variability of the epitope recognized by the neutralizing gp41 antibody 2F5," AIDS 10:587-593 (1996).

Reimann, Keith A. et al., "A Chimeric Simian/Human Immunodeficiency Virus Expressing a Primary Patient Human Immunodeficiency Virus Type 1 Isolate env Causes an AIDS-Like Disease after In Vivo Passage in Rhesus Monkeys," J. Virology 70(10):6922-6928 (1996).

Richman, Douglas D., "Nailing down another HIV target," Nature Medicine 4(11):1232-1233 (1998).

Rimsky, Laurence T. et al., "Determinants of Human Immunodeficiency Virus Type 1 Resistance to gp41-Derived Inhibitory Peptides," J. Virology 72(2):986-993 (1998).

Ring, Christine S., et al., "Structure-based Inhibitor Design by Using Protein Models for the Development of Antiparasitic Agents," Proc. Natl. Acad. Sci. USA, 90:3583-3587 (1993).

Root, Michael J. et al., "Protein Design of an HIV-1 Entry Inhibitor," Science 291:884-888 (2001).

Schumacher, Ton N.M. et al., "Identification of D-Peptide Ligands Through Mirror-Image Phage Display," Science 271:1854-1857 (1996).

Shuker, Suzanne B. et al., "Discovering High-Affinity Ligands for Proteins: SAR by NMR," Science 274:1531-1534 (1996).

Singh, Mona et al., "LearnCoil-VMF: Computational Evidence for Coiled-coil-like Motifs in Many Viral Membrane-fusion Proteins," J. Mol. Biol. 290:1031-1041 (1999).

Tan, Kemin et al., "Atomic structure of a thermostable subdomain of HIV-1 gp41," Proc. Natl. Acad. Sci. USA 94:12303-12308 (1997).

Tarrago-Litvak, Laura et al., "The reverse transcriptase of HIV-1: from enzymology to therapeutic intervention," FASEB J. 8:497-503 (1994).

Tucker, Thomas J. et al., "Development of Nonnucleoside HIV Reverse Transcriptase Inhibitors," Methods in Enzymology 275:440-472 (1996).

Tyagi, Sanjay et al., "Multicolor molecular beacons for allele discrimination," Nature Biotechnology 16:49-53 (1998).

Weissenhorn, Winfried et al., "Assembly of a rod-shaped chimera of a trimeric GCN4 zipper and the HIV-1 gp41 ectodomain expressed in *Escherichia coli*," Proc. Natl. Acad. Sci. USA 94:6065-6069 (1997).

Weissenhorn, W. et al., "Atomic structure of the ectodomain from HIV-1 gp41," Nature 387:426-430 (1997).

Weissenhorn, Winfried et al., "Crystal Structure of the Ebola Virus Membrane Fusion Subunit, GP2, from the Envelope Glycoprotein Ectodomain," Molecular Cell 2:605-616 (1998).

Wild, Carl et al., "A synthetic peptide inhibitor of human immunodeficiency virus replication: Correlation between solution structure and viral inhibition," Proc. Natl. Acad. Sci. USA 89:10537-10541 (1992).

Wild, Carl T. et al., "Peptides corresponding to a predictive -helical domain of human immunodeficiency virus type 1 gp41 are potent inhibitors of virus infection," Proc. Natl. Acad. Sci. USA 91:9770-9774 (1994).

Williams, Kelly P. et al., "Bioactive and nuclease-resistant 1-DNA ligand of vasopressin," Proc. Natl. Acad. Sci. USA 94:11285-11290 (1997).

Youngquist, R. Scott et al., "Generation and Screening of Combinatorial Peptide Libraries Designed for Rapid Sequencing by Mass Spectrometry," J. Am. Chem. Soc. 117:3900-3906 (1995).

Malashkevich, Vladimir N. et al., "Core structure of the envelope glycoprotein GP2 from Ebola virus at 1.9- resolution," Proc. Natl. Acad. Sci. USA 96:2662-2667 (1999).

Ferrer, Marc et al., "Selection of gp41-mediated HIV-1 cell entry inihibitors from biased combinatorial libraries of non-natural binding elements," Nature Structural Biology 6(10):953-960 (1999).

Jiang, Shibo et al., "Development of HIV Entry Inhibitors Targeted to the Coiled-Coil Regions of gp41," Biochemical and Biophysical Research Communications 269(3):641-646 (2000).

Yang, Xinzhen et al., "Characterization of Stable, Soluble Trimers Containing Complete Ectodomains of Human Immunodeficiency Virus Type 1 Envelope Glycoproteins," J. Virol. 74(12):5716-5725 (2000).

Bahbouhi, B., et al., "Effects of L-and D-REKR Amino Acid-Containing Peptides on HIV and SIV Envelope Glycoprotein Precursor Maturation and HIV and SIV Replication," Biochem. J. 366 (Pt. 3):863-872 (2002).

Benkirane, M., et al., "Antigenicity and Immunogenicity of Modified Synthetic Peptides Containing D-Amino Acid Residues. Antibodies to a D-Enantiomer Do Recognize the Parent L-Hexapeptide and Reciprocally," J. Biol. Chem. 268(35): 26279-26285 (1993).

Corigliano-Murphy, M.A., et al., "Synthesis and Properties of an All-D Model Ribonuclease S-Peptide," Int. J. Pep. Prot. Res. 25:225-231 (1985).

Kramer, A., et al., "Stepwise Transformation of a Cholera Toxin and a p24 (HIV-1) Epitope Into D-Peptide Analogs," Prot. Engin. 11(10):941-948 (1998).

Levy, R.B., et al., "T Lymphocytes Can Recognize Determinants Unique to Neuropeptides of Guinea Pig Myelin Basic Protein Containing a Single d-Isomer Amino Acid Substitution," J. Neuro. Res. 25(1):29-38 (1990).

Weng, Y., et al., "Mutational Analysis of Residues in the Coiled-Coil Domain of Human Immunodeficiency Virus Type 1 Transmemebrane Protein gp41," J. Virol. 72(12):9679-9682 (Abstract).

Bowie, J.U., et al., "Deciphering the Message in Protein Sequences: Tolerance to Amino Acid Substitutions," Science, 247: 1306-1310 (1990).

Chang, Ding-Kwo, et al. "Proline Affects Oligomerization of a Coiled Coil by Inducing a Kink in a Long Helix," J. Structural Biology, 128: 270-279 (1999).

Poumbouris, Pantelis, et al., "Human Immunodeficiency Virus Type 1 Envelope Glycoprotein Oligomerozation Requires the gp41 Amphipathic α-Helical/Leucine Zipper-Like Sequence," J. Virology, 71(3):2041-2049 (1997).

Bernstein, Helene B., et al., "Oligomerization of the Hydrophobic Heptad Repeat of gp41," J. Virology, 69(5): 2745-2750 (1995).

Eckert, Debra M. and Kim, Peter S., "Mechanisms of Viral Membrane Fusion and Its Inhibition," Annual Rev. Biochem 70: 777-810 (2001).

Richman, Douglas, D. et al., "Rapid Evolution of the neutralizing antibody response to HIV type 1 infection," *Proc.Natl.Acad.Sci.*, 100(7):4144-4149 (2003).

Fahey, J.L. and Schooley, R., "Status of immune-based therapies in HIV infection and AIDS", *Clin Exp. Immunol.*, 88:1-5 (1992).

Butto, S., D.A., et al., "Dual infection with different strains of the same HIV-1 subtype", AIDS, vol. II, No. 5, (1997).

Rudinger, "Peptide Hormones," (Ed. JA Parsons, Jun. 1976) pp. 1-6.

Miller, M.D., "A Human Monoclonal Antibody Blocks HIV Entry by a T20-Like Mechanism," Abstract presented at the 13th International HIV Drug Resistance Workshop, Jun. 8-12, 2004, Tenerife, Canary Islands, Spain.

Joyce, J. G., et al., "Enhancement of α-Helicity in the HIV-1 Inhibitory Peptide DP178 Leads to an Increased Affinity for Human Monoclonal Antibody 2Fs but Does Not Elicit Neutralizing Responses in Vitro," *Journal of Biological Chemistry* 277(48):45811-45820 (2002).

Moschella, F., et al., "Administration of Different Antigenic Forms of Altered Peptide Ligands Derived from HIV-1 Rtase Influences their Effects on T Helper Cell Activation," *Hum. Immunol.* 64:1-8 (2003).

Manchester, M., et al., "Identification of Temperature-Sensitive Mutants of the Human Immunodeficiency Virus Type 1 Protease through Saturation Mutagenesis," *J. Biol. Chem.*, 269(10):7689-7695 (1994).

Miller, M.D., "A Human Monoclonal Antibody Neutralizes Diverse HIV-1 Isolates by Binding a Critical gp41 Epitope," *PNAS USA* 102:14759-14764 (2005).

```
CRYST1    49.500   49.500   55.300  90.00  90.00 120.00 P 3 2 1       6
ORIGX1      1.000000  0.000000  0.000000        0.00000
ORIGX2      0.000000  1.000000  0.000000        0.00000
ORIGX3      0.000000  0.000000  1.000000        0.00000
SCALE1      0.020202  0.011664  0.000000        0.00000
SCALE2      0.000000  0.023327  0.000000        0.00000
SCALE3      0.000000  0.000000  0.018083        0.00000
HETATM    1   C   ACE N   0      19.211  14.270 -17.472  1.00 56.26           C
HETATM    2   O   ACE N   0      19.488  14.580 -16.305  1.00 56.37           O
HETATM    3   CH3 ACE N   0      20.273  14.045 -18.531  1.00 56.01           C
ATOM      4   N   SER N 546      17.955  14.014 -17.827  1.00 56.49           N
ATOM      5   CA  SER N 546      16.876  14.392 -16.942  1.00 56.15           C
ATOM      6   C   SER N 546      16.909  13.631 -15.655  1.00 56.24           C
ATOM      7   O   SER N 546      16.736  14.255 -14.615  1.00 57.67           O
ATOM      8   CB  SER N 546      15.525  14.172 -17.546  1.00 56.05           C
ATOM      9   OG  SER N 546      15.498  12.815 -17.842  1.00 57.84           O
ATOM     10   H   SER N 546      17.816  13.501 -18.552  1.00  0.00           H
ATOM     11   HG  SER N 546      15.988  12.455 -18.582  1.00  0.00           H
ATOM     12   N   GLY N 547      17.181  12.316 -15.724  1.00 55.59           N
ATOM     13   CA  GLY N 547      17.202  11.414 -14.570  1.00 53.04           C
ATOM     14   C   GLY N 547      18.299  11.783 -13.596  1.00 51.70           C
ATOM     15   O   GLY N 547      18.147  11.667 -12.391  1.00 50.76           O
ATOM     16   H   GLY N 547      17.409  11.945 -16.618  1.00  0.00           H
ATOM     17   N   ILE N 548      19.399  12.280 -14.145  1.00 51.57           N
ATOM     18   CA  ILE N 548      20.551  12.815 -13.425  1.00 52.14           C
ATOM     19   C   ILE N 548      20.218  14.116 -12.696  1.00 51.31           C
ATOM     20   O   ILE N 548      20.543  14.273 -11.519  1.00 50.83           O
ATOM     21   CB  ILE N 548      21.693  13.043 -14.436  1.00 54.22           C
ATOM     22   CG1 ILE N 548      22.120  11.712 -15.087  1.00 54.58           C
ATOM     23   CG2 ILE N 548      22.861  13.705 -13.721  1.00 55.25           C
ATOM     24   CD1 ILE N 548      23.126  11.909 -16.234  1.00 56.29           C
ATOM     25   H   ILE N 548      19.445  12.272 -15.118  1.00  0.00           H
ATOM     26   N   VAL N 549      19.590  15.054 -13.393  1.00 50.93           N
ATOM     27   CA  VAL N 549      19.093  16.291 -12.786  1.00 50.79           C
ATOM     28   C   VAL N 549      18.036  15.977 -11.726  1.00 50.36           C
ATOM     29   O   VAL N 549      17.992  16.598 -10.674  1.00 51.60           O
ATOM     30   CB  VAL N 549      18.451  17.196 -13.841  1.00 52.28           C
ATOM     31   CG1 VAL N 549      17.814  18.437 -13.226  1.00 54.97           C
ATOM     32   CG2 VAL N 549      19.539  17.650 -14.780  1.00 51.05           C
ATOM     33   H   VAL N 549      19.486  14.911 -14.360  1.00  0.00           H
ATOM     34   N   GLN N 550      17.187  15.030 -12.001  1.00 49.13           N
ATOM     35   CA  GLN N 550      16.176  14.508 -11.109  1.00 49.23           C
ATOM     36   C   GLN N 550      16.843  13.895  -9.861  1.00 48.50           C
ATOM     37   O   GLN N 550      16.520  14.236  -8.736  1.00 47.94           O
ATOM     38   CB  GLN N 550      15.452  13.398 -11.814  1.00 52.96           C
ATOM     39   CG  GLN N 550      13.929  13.475 -11.925  1.00 60.75           C
ATOM     40   CD  GLN N 550      13.343  13.742 -10.585  1.00 65.31           C
ATOM     41   OE1 GLN N 550      13.048  14.884 -10.294  1.00 71.73           O
ATOM     42   NE2 GLN N 550      13.111  12.750  -9.753  1.00 67.42           N
ATOM     43   H   GLN N 550      17.256  14.628 -12.913  1.00  0.00           H
ATOM     44   1HE2 GLN N 550     12.689  12.960  -8.892  1.00  0.00           H
ATOM     45   2HE2 GLN N 550     13.298  11.810 -10.020  1.00  0.00           H
ATOM     46   N   GLN N 551      17.847  13.009 -10.014  1.00 47.87           N
ATOM     47   CA  GLN N 551      18.607  12.368  -8.940  1.00 47.02           C
ATOM     48   C   GLN N 551      19.320  13.416  -8.092  1.00 45.81           C
ATOM     49   O   GLN N 551      19.330  13.334  -6.868  1.00 46.09           O
ATOM     50   CB  GLN N 551      19.605  11.378  -9.582  1.00 45.66           C
ATOM     51   CG  GLN N 551      20.600  10.535  -8.719  1.00 41.50           C
```

FIG. 5A

| | | | | | | | | | |
|---|---|---|---|---|---|---|---|---|---|
| ATOM | 52 | CD | GLN | N | 551 | 19.994 | 9.589 | -7.719 | 1.00 39.83 | C |
| ATOM | 53 | OE1 | GLN | N | 551 | 18.955 | 9.872 | -7.134 | 1.00 42.03 | O |
| ATOM | 54 | NE2 | GLN | N | 551 | 20.573 | 8.430 | -7.469 | 1.00 34.15 | N |
| ATOM | 55 | H | GLN | N | 551 | 18.103 | 12.786 | -10.928 | 1.00 0.00 | H |
| ATOM | 56 | 1HE2 | GLN | N | 551 | 20.183 | 7.817 | -6.808 | 1.00 0.00 | H |
| ATOM | 57 | 2HE2 | GLN | N | 551 | 21.382 | 8.205 | -7.988 | 1.00 0.00 | H |
| ATOM | 58 | N | GLN | N | 552 | 19.874 | 14.445 | -8.725 | 1.00 45.32 | N |
| ATOM | 59 | CA | GLN | N | 552 | 20.538 | 15.562 | -8.041 | 1.00 44.72 | C |
| ATOM | 60 | C | GLN | N | 552 | 19.620 | 16.316 | -7.096 | 1.00 43.57 | C |
| ATOM | 61 | O | GLN | N | 552 | 19.987 | 16.732 | -6.006 | 1.00 41.76 | O |
| ATOM | 62 | CB | GLN | N | 552 | 21.115 | 16.542 | -9.078 | 1.00 46.04 | C |
| ATOM | 63 | CG | GLN | N | 552 | 22.500 | 16.015 | -9.433 | 1.00 50.92 | C |
| ATOM | 64 | CD | GLN | N | 552 | 23.257 | 16.787 | -10.486 | 1.00 54.67 | C |
| ATOM | 65 | OE1 | GLN | N | 552 | 22.658 | 17.525 | -11.260 | 1.00 59.31 | O |
| ATOM | 66 | NE2 | GLN | N | 552 | 24.575 | 16.670 | -10.575 | 1.00 56.36 | N |
| ATOM | 67 | H | GLN | N | 552 | 19.818 | 14.442 | -9.707 | 1.00 0.00 | H |
| ATOM | 68 | 1HE2 | GLN | N | 552 | 24.996 | 17.210 | -11.277 | 1.00 0.00 | H |
| ATOM | 69 | 2HE2 | GLN | N | 552 | 25.079 | 16.087 | -9.993 | 1.00 0.00 | H |
| ATOM | 70 | N | ASN | N | 553 | 18.383 | 16.452 | -7.534 | 1.00 43.26 | N |
| ATOM | 71 | CA | ASN | N | 553 | 17.350 | 17.053 | -6.728 | 1.00 43.57 | C |
| ATOM | 72 | C | ASN | N | 553 | 17.047 | 16.173 | -5.554 | 1.00 42.82 | C |
| ATOM | 73 | O | ASN | N | 553 | 16.914 | 16.649 | -4.433 | 1.00 43.18 | O |
| ATOM | 74 | CB | ASN | N | 553 | 16.050 | 17.238 | -7.509 | 1.00 46.51 | C |
| ATOM | 75 | CG | ASN | N | 553 | 15.095 | 18.168 | -6.803 | 1.00 51.48 | C |
| ATOM | 76 | OD1 | ASN | N | 553 | 15.256 | 18.608 | -5.669 | 1.00 59.01 | O |
| ATOM | 77 | ND2 | ASN | N | 553 | 14.006 | 18.540 | -7.412 | 1.00 57.62 | N |
| ATOM | 78 | H | ASN | N | 553 | 18.168 | 16.200 | -8.470 | 1.00 0.00 | H |
| ATOM | 79 | 1HD2 | ASN | N | 553 | 13.333 | 19.036 | -6.902 | 1.00 0.00 | H |
| ATOM | 80 | 2HD2 | ASN | N | 553 | 13.822 | 18.181 | -8.313 | 1.00 0.00 | H |
| ATOM | 81 | N | ASN | N | 554 | 17.005 | 14.883 | -5.807 | 1.00 42.25 | N |
| ATOM | 82 | CA | ASN | N | 554 | 16.731 | 13.930 | -4.736 | 1.00 43.15 | C |
| ATOM | 83 | C | ASN | N | 554 | 17.876 | 13.908 | -3.715 | 1.00 42.63 | C |
| ATOM | 84 | O | ASN | N | 554 | 17.628 | 13.893 | -2.508 | 1.00 42.65 | O |
| ATOM | 85 | CB | ASN | N | 554 | 16.534 | 12.538 | -5.331 | 1.00 44.49 | C |
| ATOM | 86 | CG | ASN | N | 554 | 15.340 | 12.520 | -6.239 | 1.00 48.97 | C |
| ATOM | 87 | OD1 | ASN | N | 554 | 14.277 | 13.033 | -5.925 | 1.00 51.91 | O |
| ATOM | 88 | ND2 | ASN | N | 554 | 15.485 | 12.022 | -7.460 | 1.00 52.70 | N |
| ATOM | 89 | H | ASN | N | 554 | 17.137 | 14.573 | -6.736 | 1.00 0.00 | H |
| ATOM | 90 | 1HD2 | ASN | N | 554 | 14.691 | 11.924 | -8.059 | 1.00 0.00 | H |
| ATOM | 91 | 2HD2 | ASN | N | 554 | 16.321 | 11.585 | -7.671 | 1.00 0.00 | H |
| ATOM | 92 | N | LEU | N | 555 | 19.125 | 14.034 | -4.177 | 1.00 41.19 | N |
| ATOM | 93 | CA | LEU | N | 555 | 20.270 | 14.065 | -3.310 | 1.00 39.88 | C |
| ATOM | 94 | C | LEU | N | 555 | 20.274 | 15.341 | -2.498 | 1.00 40.16 | C |
| ATOM | 95 | O | LEU | N | 555 | 20.383 | 15.280 | -1.272 | 1.00 40.42 | O |
| ATOM | 96 | CB | LEU | N | 555 | 21.556 | 13.984 | -4.115 | 1.00 37.85 | C |
| ATOM | 97 | CG | LEU | N | 555 | 21.762 | 12.724 | -4.945 | 1.00 38.85 | C |
| ATOM | 98 | CD1 | LEU | N | 555 | 23.106 | 12.783 | -5.687 | 1.00 39.10 | C |
| ATOM | 99 | CD2 | LEU | N | 555 | 21.643 | 11.526 | -4.019 | 1.00 36.44 | C |
| ATOM | 100 | H | LEU | N | 555 | 19.245 | 14.101 | -5.145 | 1.00 0.00 | H |
| ATOM | 101 | N | LEU | N | 556 | 20.097 | 16.504 | -3.139 | 1.00 39.83 | N |
| ATOM | 102 | CA | LEU | N | 556 | 20.056 | 17.800 | -2.490 | 1.00 39.00 | C |
| ATOM | 103 | C | LEU | N | 556 | 18.997 | 17.825 | -1.428 | 1.00 40.28 | C |
| ATOM | 104 | O | LEU | N | 556 | 19.251 | 18.290 | -0.326 | 1.00 40.24 | O |
| ATOM | 105 | CB | LEU | N | 556 | 19.769 | 18.896 | -3.504 | 1.00 37.52 | C |
| ATOM | 106 | CG | LEU | N | 556 | 19.826 | 20.327 | -2.982 | 1.00 35.51 | C |
| ATOM | 107 | CD1 | LEU | N | 556 | 21.227 | 20.634 | -2.595 | 1.00 38.30 | C |
| ATOM | 108 | CD2 | LEU | N | 556 | 19.383 | 21.304 | -4.051 | 1.00 35.56 | C |
| ATOM | 109 | H | LEU | N | 556 | 20.042 | 16.470 | -4.118 | 1.00 0.00 | H |

FIG. 5B

```
ATOM    110  N    ARG N  557     17.823  17.292  -1.689  1.00 41.01           N
ATOM    111  CA   ARG N  557     16.776  17.288  -0.685  1.00 42.31           C
ATOM    112  C    ARG N  557     17.200  16.394   0.467  1.00 42.26           C
ATOM    113  O    ARG N  557     17.012  16.740   1.622  1.00 42.69           O
ATOM    114  CB   ARG N  557     15.457  16.809  -1.356  1.00 45.42           C
ATOM    115  CG   ARG N  557     14.746  17.951  -2.111  1.00 50.30           C
ATOM    116  CD   ARG N  557     13.344  17.553  -2.601  1.00 57.56           C
ATOM    117  NE   ARG N  557     13.280  16.625  -3.751  1.00 64.22           N
ATOM    118  CZ   ARG N  557     12.355  15.631  -3.918  1.00 63.91           C
ATOM    119  NH1  ARG N  557     11.397  15.396  -3.011  1.00 64.47           N
ATOM    120  NH2  ARG N  557     12.335  14.867  -5.036  1.00 59.98           N
ATOM    121  H    ARG N  557     17.638  16.953  -2.607  1.00  0.00           H
ATOM    122  HE   ARG N  557     13.950  16.746  -4.463  1.00  0.00           H
ATOM    123  1HH1 ARG N  557     11.350  15.933  -2.167  1.00  0.00           H
ATOM    124  2HH1 ARG N  557     10.752  14.634  -3.142  1.00  0.00           H
ATOM    125  1HH2 ARG N  557     12.994  15.016  -5.779  1.00  0.00           H
ATOM    126  2HH2 ARG N  557     11.659  14.126  -5.135  1.00  0.00           H
ATOM    127  N    ALA N  558     17.915  15.313   0.192  1.00 41.57           N
ATOM    128  CA   ALA N  558     18.387  14.409   1.226  1.00 41.10           C
ATOM    129  C    ALA N  558     19.392  15.061   2.144  1.00 40.54           C
ATOM    130  O    ALA N  558     19.295  14.930   3.360  1.00 39.05           O
ATOM    131  CB   ALA N  558     19.030  13.199   0.587  1.00 41.90           C
ATOM    132  H    ALA N  558     18.173  15.144  -0.746  1.00  0.00           H
ATOM    133  N    ILE N  559     20.294  15.861   1.569  1.00 41.09           N
ATOM    134  CA   ILE N  559     21.309  16.634   2.316  1.00 40.49           C
ATOM    135  C    ILE N  559     20.614  17.708   3.169  1.00 41.59           C
ATOM    136  O    ILE N  559     20.961  17.946   4.334  1.00 41.89           O
ATOM    137  CB   ILE N  559     22.333  17.310   1.315  1.00 37.40           C
ATOM    138  CG1  ILE N  559     23.112  16.223   0.558  1.00 35.03           C
ATOM    139  CG2  ILE N  559     23.294  18.213   2.061  1.00 36.22           C
ATOM    140  CD1  ILE N  559     23.944  16.723  -0.634  1.00 29.22           C
ATOM    141  H    ILE N  559     20.362  15.968   0.586  1.00  0.00           H
ATOM    142  N    GLU N  560     19.595  18.377   2.634  1.00 41.05           N
ATOM    143  CA   GLU N  560     18.927  19.411   3.378  1.00 41.53           C
ATOM    144  C    GLU N  560     18.194  18.774   4.529  1.00 41.42           C
ATOM    145  O    GLU N  560     18.199  19.290   5.659  1.00 42.58           O
ATOM    146  CB   GLU N  560     17.950  20.139   2.504 -1.00 42.94           C
ATOM    147  CG   GLU N  560     18.559  20.916   1.342  1.00 49.98           C
ATOM    148  CD   GLU N  560     17.569  21.635   0.403  1.00 56.47           C
ATOM    149  OE1  GLU N  560     16.353  21.580   0.624  1.00 58.21           O
ATOM    150  OE2  GLU N  560     18.018  22.257  -0.566  1.00 56.22           O
ATOM    151  H    GLU N  560     19.338  18.191   1.696  1.00  0.00           H
ATOM    152  N    ALA N  561     17.505  17.606   4.311  1.00 41.55           N
ATOM    153  CA   ALA N  561     16.886  16.905   5.362  1.00 41.77           C
ATOM    154  C    ALA N  561     17.880  16.505   6.441  1.00 42.70           C
ATOM    155  O    ALA N  561     17.661  16.726   7.641  1.00 42.40           O
ATOM    156  CB   ALA N  561     16.221  15.671   4.797  1.00 39.29           C
ATOM    157  H    ALA N  561     17.617  17.230   3.403  1.00  0.00           H
ATOM    158  N    GLN N  562     19.053  16.076   6.014  1.00 43.26           N
ATOM    159  CA   GLN N  562     20.042  15.666   6.986  1.00 43.97           C
ATOM    160  C    GLN N  562     20.607  16.819   7.771  1.00 43.53           C
ATOM    161  O    GLN N  562     20.989  16.658   8.934  1.00 43.63           O
ATOM    162  CB   GLN N  562     21.194  14.960   6.319  1.00 45.81           C
ATOM    163  CG   GLN N  562     20.703  13.620   5.857  1.00 48.45           C
ATOM    164  CD   GLN N  562     21.844  12.875   5.276  1.00 52.27           C
ATOM    165  OE1  GLN N  562     22.693  13.426   4.578  1.00 54.50           O
ATOM    166  NE2  GLN N  562     21.828  11.590   5.556  1.00 54.42           N
ATOM    167  H    GLN N  562     19.263  16.023   5.043  1.00  0.00           H
```

FIG. 5C

```
ATOM    168  1HE2 GLN N 562      22.558   11.067    5.175  1.00  0.00           H
ATOM    169  2HE2 GLN N 562      21.094   11.246    6.104  1.00  0.00           H
ATOM    170   N   GLN N 563      20.651   17.976    7.121  1.00 42.95           N
ATOM    171   CA  GLN N 563      21.100   19.166    7.761  1.00 43.75           C
ATOM    172   C   GLN N 563      20.156   19.484    8.886  1.00 44.90           C
ATOM    173   O   GLN N 563      20.607   19.846    9.965  1.00 45.57           O
ATOM    174   CB  GLN N 563      21.149   20.323    6.777  1.00 41.93           C
ATOM    175   CG  GLN N 563      21.818   21.547    7.400  1.00 41.15           C
ATOM    176   CD  GLN N 563      23.189   21.261    8.013  1.00 42.08           C
ATOM    177   OE1 GLN N 563      23.917   20.363    7.583  1.00 48.51           O
ATOM    178   NE2 GLN N 563      23.627   21.967    9.043  1.00 39.35           N
ATOM    179   H   GLN N 563      20.474   17.971    6.162  1.00  0.00           H
ATOM    180  1HE2 GLN N 563      24.526   21.732    9.369  1.00  0.00           H
ATOM    181  2HE2 GLN N 563      23.085   22.653    9.451  1.00  0.00           H
ATOM    182   N   HIS N 564      18.842   19.364    8.714  1.00 46.08           N
ATOM    183   CA  HIS N 564      17.909   19.582    9.830  1.00 47.34           C
ATOM    184   C   HIS N 564      18.133   18.647   10.985  1.00 46.35           C
ATOM    185   O   HIS N 564      18.167   19.105   12.118  1.00 45.28           O
ATOM    186   CB  HIS N 564      16.508   19.405    9.372  1.00 52.29           C
ATOM    187   CG  HIS N 564      16.122   20.497    8.389  1.00 58.12           C
ATOM    188   ND1 HIS N 564      15.024   20.554    7.683  1.00 63.16           N
ATOM    189   CD2 HIS N 564      16.858   21.617    8.051  1.00 61.99           C
ATOM    190   CE1 HIS N 564      15.029   21.609    6.945  1.00 62.90           C
ATOM    191   NE2 HIS N 564      16.140   22.240    7.177  1.00 62.40           N
ATOM    192   H   HIS N 564      18.535   19.251    7.783 -1.00  0.00           H
ATOM    193   HD1 HIS N 564      14.318   19.929    7.750  1.00  0.00           H
ATOM    194   HE2 HIS N 564      16.408   23.027    6.657  1.00  0.00           H
ATOM    195   N   LEU N 565      18.352   17.382   10.651  1.00 46.30           N
ATOM    196   CA  LEU N 565      18.728   16.389   11.627  1.00 47.50           C
ATOM    197   C   LEU N 565      20.023   16.771   12.360  1.00 47.96           C
ATOM    198   O   LEU N 565      20.106   16.694   13.603  1.00 47.27           O
ATOM    199   CB  LEU N 565      18.955   15.028   10.980  1.00 48.98           C
ATOM    200   CG  LEU N 565      17.893   13.938   10.810  1.00 50.24           C
ATOM    201   CD1 LEU N 565      18.612   13.580   10.876  1.00 49.28           C
ATOM    202   CD2 LEU N 565      16.843   13.985   11.920  1.00 52.14           C
ATOM    203   H   LEU N 565      18.325   17.139    9.702  1.00  0.00           H
ATOM    204   N   LEU N 566      21.033   17.258   11.622  1.00 47.51           N
ATOM    205   CA  LEU N 566      22.278   17.718   12.239  1.00 48.90           C
ATOM    206   C   LEU N 566      22.041   18.835   13.232  1.00 48.39           C
ATOM    207   O   LEU N 566      22.563   18.779   14.346  1.00 47.61           O
ATOM    208   CB  LEU N 566      23.299   18.205   11.144  1.00 50.19           C
ATOM    209   CG  LEU N 566      24.223   17.163   10.521  1.00 50.83           C
ATOM    210   CD1 LEU N 566      24.767   17.627    9.151  1.00 45.73           C
ATOM    211   CD2 LEU N 566      25.295   16.848   11.579  1.00 50.95           C
ATOM    212   H   LEU N 566      20.921   17.339   10.658  1.00  0.00           H
ATOM    213   N   GLN N 567      21.182   19.797   12.902  1.00 48.03           N
ATOM    214   CA  GLN N 567      20.839   20.897   13.794  1.00 48.69           C
ATOM    215   C   GLN N 567      20.124   20.425   15.041  1.00 48.44           C
ATOM    216   O   GLN N 567      20.379   20.878   16.165  1.00 48.89           O
ATOM    217   CB  GLN N 567      19.940   21.927   13.071  1.00 49.47           C
ATOM    218   CG  GLN N 567      20.632   22.647   11.906  1.00 56.49           C
ATOM    219   CD  GLN N 567      21.964   23.290   12.278  1.00 63.24           C
ATOM    220   OE1 GLN N 567      22.393   23.265   13.426  1.00 66.99           O
ATOM    221   NE2 GLN N 567      22.723   23.924   11.394  1.00 68.66           N
ATOM    222   H   GLN N 567      20.769   19.768   12.006  1.00  0.00           H
ATOM    223  1HE2 GLN N 567      23.539   24.303   11.833  1.00  0.00           H
ATOM    224  2HE2 GLN N 567      22.514   24.033   10.471  1.00  0.00           H
ATOM    225   N   LEU N 568      19.313   19.365   14.871  1.00 48.05           N
```

FIG. 5D

| | | | | | | | | | |
|---|---|---|---|---|---|---|---|---|---|
| ATOM | 226 | CA | LEU | N | 568 | 18.513 | 18.907 | 15.980 | 1.00 47.97 | C |
| ATOM | 227 | C | LEU | N | 568 | 19.410 | 18.201 | 16.958 | 1.00 47.65 | C |
| ATOM | 228 | O | LEU | N | 568 | 19.319 | 18.457 | 18.167 | 1.00 48.06 | O |
| ATOM | 229 | CB | LEU | N | 568 | 17.399 | 18.019 | 15.472 | 1.00 47.11 | C |
| ATOM | 230 | CG | LEU | N | 568 | 16.441 | 18.651 | 14.453 | 1.00 52.05 | C |
| ATOM | 231 | CD1 | LEU | N | 568 | 15.376 | 17.669 | 14.033 | 1.00 49.38 | C |
| ATOM | 232 | CD2 | LEU | N | 568 | 15.844 | 19.917 | 15.044 | 1.00 53.06 | C |
| ATOM | 233 | H | LEU | N | 568 | 19.352 | 18.869 | 14.024 | 1.00 0.00 | H |
| ATOM | 234 | N | THR | N | 569 | 20.343 | 17.385 | 16.474 | 1.00 47.68 | N |
| ATOM | 235 | CA | THR | N | 569 | 21.300 | 16.706 | 17.345 | 1.00 46.82 | C |
| ATOM | 236 | C | THR | N | 569 | 22.179 | 17.733 | 18.051 | 1.00 46.78 | C |
| ATOM | 237 | O | THR | N | 569 | 22.428 | 17.562 | 19.238 | 1.00 46.53 | O |
| ATOM | 238 | CB | THR | N | 569 | 22.196 | 15.706 | 16.513 | 1.00 48.47 | C |
| ATOM | 239 | OG1 | THR | N | 569 | 22.896 | 16.453 | 15.512 | 1.00 50.39 | O |
| ATOM | 240 | CG2 | THR | N | 569 | 21.367 | 14.574 | 15.887 | 1.00 45.02 | C |
| ATOM | 241 | H | THR | N | 569 | 20.365 | 17.208 | 15.510 | 1.00 0.00 | H |
| ATOM | 242 | HG1 | THR | N | 569 | 22.309 | 16.916 | 14.917 | 1.00 0.00 | H |
| ATOM | 243 | N | VAL | N | 570 | 22.568 | 18.851 | 17.411 | 1.00 46.51 | N |
| ATOM | 244 | CA | VAL | N | 570 | 23.388 | 19.879 | 18.056 | 1.00 46.07 | C |
| ATOM | 245 | C | VAL | N | 570 | 22.584 | 20.543 | 19.173 | 1.00 46.10 | C |
| ATOM | 246 | O | VAL | N | 570 | 23.109 | 20.791 | 20.268 | 1.00 46.19 | O |
| ATOM | 247 | CB | VAL | N | 570 | 23.824 | 20.975 | 17.067 | 1.00 46.87 | C |
| ATOM | 248 | CG1 | VAL | N | 570 | 24.628 | 22.078 | 17.767 | 1.00 43.56 | C |
| ATOM | 249 | CG2 | VAL | N | 570 | 24.698 | 20.324 | 16.003 | 1.00 47.58 | C |
| ATOM | 250 | H | VAL | N | 570 | 22.267 | 19.018 | 16.480 | 1.00 0.00 | H |
| ATOM | 251 | N | TRP | N | 571 | 21.311 | 20.824 | 18.901 | 1.00 44.96 | N |
| ATOM | 252 | CA | TRP | N | 571 | 20.448 | 21.354 | 19.916 | 1.00 45.54 | C |
| ATOM | 253 | C | TRP | N | 571 | 20.408 | 20.357 | 21.079 | 1.00 45.70 | C |
| ATOM | 254 | O | TRP | N | 571 | 20.466 | 20.796 | 22.237 | 1.00 46.48 | O |
| ATOM | 255 | CB | TRP | N | 571 | 19.025 | 21.547 | 19.422 | 1.00 45.68 | C |
| ATOM | 256 | CG | TRP | N | 571 | 18.046 | 21.979 | 20.538 | 1.00 47.31 | C |
| ATOM | 257 | CD1 | TRP | N | 571 | 17.853 | 23.309 | 20.778 | 1.00 47.86 | C |
| ATOM | 258 | CD2 | TRP | N | 571 | 17.291 | 21.171 | 21.401 | 1.00 48.92 | C |
| ATOM | 259 | NE1 | TRP | N | 571 | 16.991 | 23.361 | 21.767 | 1.00 47.92 | N |
| ATOM | 260 | CE2 | TRP | N | 571 | 16.630 | 22.132 | 22.175 | 1.00 47.99 | C |
| ATOM | 261 | CE3 | TRP | N | 571 | 17.056 | 19.805 | 21.674 | 1.00 48.37 | C |
| ATOM | 262 | CZ2 | TRP | N | 571 | 15.742 | 21.753 | 23.189 | 1.00 46.81 | C |
| ATOM | 263 | CZ3 | TRP | N | 571 | 16.181 | 19.419 | 22.697 | 1.00 46.38 | C |
| ATOM | 264 | CH2 | TRP | N | 571 | 15.524 | 20.395 | 23.451 | 1.00 47.44 | C |
| ATOM | 265 | H | TRP | N | 571 | 20.993 | 20.625 | 17.998 | 1.00 0.00 | H |
| ATOM | 266 | HE1 | TRP | N | 571 | 16.632 | 24.201 | 22.162 | 1.00 0.00 | H |
| ATOM | 267 | N | GLY | N | 572 | 20.356 | 19.036 | 20.642 | 1.00 45.29 | N |
| ATOM | 268 | CA | GLY | N | 572 | 20.270 | 18.034 | 21.892 | 1.00 44.49 | C |
| ATOM | 269 | C | GLY | N | 572 | 21.532 | 18.044 | 22.719 | 1.00 44.03 | C |
| ATOM | 270 | O | GLY | N | 572 | 21.491 | 18.102 | 23.948 | 1.00 43.66 | O |
| ATOM | 271 | H | GLY | N | 572 | 20.483 | 18.736 | 19.917 | 1.00 0.00 | H |
| ATOM | 272 | N | ILE | N | 573 | 22.671 | 18.122 | 22.031 | 1.00 44.11 | N |
| ATOM | 273 | CA | ILE | N | 573 | 23.986 | 18.156 | 22.666 | 1.00 44.64 | C |
| ATOM | 274 | C | ILE | N | 573 | 24.148 | 19.402 | 23.527 | 1.00 45.83 | C |
| ATOM | 275 | O | ILE | N | 573 | 24.571 | 19.300 | 24.666 | 1.00 46.58 | O |
| ATOM | 276 | CB | ILE | N | 573 | 25.125 | 18.159 | 21.622 | 1.00 44.82 | C |
| ATOM | 277 | CG1 | ILE | N | 573 | 25.094 | 16.885 | 20.810 | 1.00 43.85 | C |
| ATOM | 278 | CG2 | ILE | N | 573 | 26.482 | 18.303 | 22.325 | 1.00 44.82 | C |
| ATOM | 279 | CD1 | ILE | N | 573 | 26.010 | 16.963 | 19.585 | 1.00 44.87 | C |
| ATOM | 280 | H | ILE | N | 573 | 22.603 | 18.229 | 21.056 | 1.00 0.00 | H |
| ATOM | 281 | N | LYS | N | 574 | 23.840 | 20.594 | 23.044 | 1.00 46.57 | N |
| ATOM | 282 | CA | LYS | N | 574 | 24.001 | 21.819 | 23.817 | 1.00 47.39 | C |
| ATOM | 283 | C | LYS | N | 574 | 23.075 | 21.810 | 25.027 | 1.00 47.64 | C |

FIG. 5E

| | | | | | | | | | |
|---|---|---|---|---|---|---|---|---|---|
| ATOM | 284 | O | LYS | N | 574 | 23.456 | 22.221 | 26.103 | 1.00 47.42 | O |
| ATOM | 285 | CB | LYS | N | 574 | 23.679 | 23.041 | 22.944 | 1.00 47.81 | C |
| ATOM | 286 | CG | LYS | N | 574 | 24.626 | 23.233 | 21.776 | 1.00 47.81 | C |
| ATOM | 287 | CD | LYS | N | 574 | 24.343 | 24.597 | 21.117 | 1.00 49.66 | C |
| ATOM | 288 | CE | LYS | N | 574 | 25.235 | 24.786 | 19.879 | 1.00 57.06 | C |
| ATOM | 289 | NZ | LYS | N | 574 | 25.047 | 26.026 | 19.167 | 1.00 51.95 | N |
| ATOM | 290 | H | LYS | N | 574 | 23.447 | 20.634 | 22.137 | 1.00 0.00 | H |
| ATOM | 291 | 1HZ | LYS | N | 574 | 24.056 | 26.097 | 18.850 | 1.00 0.00 | H |
| ATOM | 292 | 2HZ | LYS | N | 574 | 25.302 | 26.787 | 19.816 | 1.00 0.00 | H |
| ATOM | 293 | 3HZ | LYS | N | 574 | 25.671 | 26.035 | 18.326 | 1.00 0.00 | H |
| ATOM | 294 | N | GLN | N | 575 | 21.863 | 21.301 | 24.898 | 1.00 47.76 | N |
| ATOM | 295 | CA | GLN | N | 575 | 20.947 | 21.160 | 26.010 | 1.00 49.56 | C |
| ATOM | 296 | C | GLN | N | 575 | 21.523 | 20.277 | 27.101 | 1.00 50.70 | C |
| ATOM | 297 | O | GLN | N | 575 | 21.530 | 20.599 | 28.288 | 1.00 50.85 | O |
| ATOM | 298 | CB | GLN | N | 575 | 19.690 | 20.480 | 25.617 | 1.00 51.27 | C |
| ATOM | 299 | CG | GLN | N | 575 | 18.703 | 21.312 | 24.814 | 1.00 53.77 | C |
| ATOM | 300 | CD | GLN | N | 575 | 18.143 | 22.472 | 25.591 | 1.00 56.45 | C |
| ATOM | 301 | OE1 | GLN | N | 575 | 17.537 | 22.387 | 26.656 | 1.00 59.04 | O |
| ATOM | 302 | NE2 | GLN | N | 575 | 18.305 | 23.636 | 25.024 | 1.00 57.29 | N |
| ATOM | 303 | H | GLN | N | 575 | 21.606 | 20.942 | 24.016 | 1.00 0.00 | H |
| ATOM | 304 | 1HE2 | GLN | N | 575 | 17.915 | 24.394 | 25.512 | 1.00 0.00 | H |
| ATOM | 305 | 2HE2 | GLN | N | 575 | 18.755 | 23.713 | 24.154 | 1.00 0.00 | H |
| ATOM | 306 | N | LEU | N | 576 | 22.054 | 19.126 | 26.704 | 1.00 52.27 | N |
| ATOM | 307 | CA | LEU | N | 576 | 22.609 | 18.227 | 27.703 | 1.00 54.14 | C |
| ATOM | 308 | C | LEU | N | 576 | 23.887 | 18.797 | 28.277 | 1.00 55.59 | C |
| ATOM | 309 | O | LEU | N | 576 | 24.135 | 18.667 | 29.472 | 1.00 55.72 | O |
| ATOM | 310 | CB | LEU | N | 576 | 22.892 | 16.841 | 27.117 | 1.00 51.84 | C |
| ATOM | 311 | CG | LEU | N | 576 | 21.688 | 16.085 | 26.553 | 1.00 52.59 | C |
| ATOM | 312 | CD1 | LEU | N | 576 | 22.138 | 14.746 | 26.001 | 1.00 50.01 | C |
| ATOM | 313 | CD2 | LEU | N | 576 | 20.643 | 15.931 | 27.638 | 1.00 51.10 | C |
| ATOM | 314 | H | LEU | N | 576 | 22.073 | 18.904 | 25.743 | 1.00 0.00 | H |
| ATOM | 315 | N | GLN | N | 577 | 24.692 | 19.489 | 27.474 | 1.00 57.40 | N |
| ATOM | 316 | CA | GLN | N | 577 | 25.921 | 20.110 | 27.929 | 1.00 59.81 | C |
| ATOM | 317 | C | GLN | N | 577 | 25.672 | 21.245 | 28.915 | 1.00 62.47 | C |
| ATOM | 318 | O | GLN | N | 577 | 26.453 | 21.404 | 29.852 | 1.00 62.30 | O |
| ATOM | 319 | CB | GLN | N | 577 | 26.708 | 20.620 | 26.730 | 1.00 57.05 | C |
| ATOM | 320 | CG | GLN | N | 577 | 28.060 | 21.087 | 27.186 | 1.00 58.22 | C |
| ATOM | 321 | CD | GLN | N | 577 | 28.180 | 22.600 | 27.330 | 1.00 60.01 | C |
| ATOM | 322 | OE1 | GLN | N | 577 | 27.202 | 23.340 | 27.358 | 1.00 60.52 | O |
| ATOM | 323 | NE2 | GLN | N | 577 | 29.385 | 23.134 | 27.363 | 1.00 61.54 | N |
| ATOM | 324 | H | GLN | N | 577 | 24.455 | 19.535 | 26.530 | 1.00 0.00 | H |
| ATOM | 325 | 1HE2 | GLN | N | 577 | 29.399 | 24.107 | 27.430 | 1.00 0.00 | H |
| ATOM | 326 | 2HE2 | GLN | N | 577 | 30.164 | 22.554 | 27.335 | 1.00 0.00 | H |
| ATOM | 327 | N | ALA | N | 578 | 24.584 | 21.997 | 28.775 | 1.00 65.04 | N |
| ATOM | 328 | CA | ALA | N | 578 | 24.312 | 23.121 | 29.647 | 1.00 67.52 | C |
| ATOM | 329 | C | ALA | N | 578 | 24.101 | 22.643 | 31.062 | 1.00 69.93 | C |
| ATOM | 330 | O | ALA | N | 578 | 24.379 | 23.346 | 32.025 | 1.00 70.22 | O |
| ATOM | 331 | CB | ALA | N | 578 | 23.056 | 23.840 | 29.207 | 1.00 66.26 | C |
| ATOM | 332 | H | ALA | N | 578 | 23.987 | 21.810 | 28.016 | 1.00 0.00 | H |
| ATOM | 333 | N | ARG | N | 579 | 23.604 | 21.407 | 31.195 | 1.00 72.80 | N |
| ATOM | 334 | CA | ARG | N | 579 | 23.277 | 20.834 | 32.491 | 1.00 76.15 | C |
| ATOM | 335 | C | ARG | N | 579 | 24.297 | 19.924 | 33.116 | 1.00 77.71 | C |
| ATOM | 336 | O | ARG | N | 579 | 24.155 | 19.391 | 34.212 | 1.00 78.20 | O |
| ATOM | 337 | CB | ARG | N | 579 | 21.939 | 20.093 | 32.368 | 1.00 77.38 | C |
| ATOM | 338 | CG | ARG | N | 579 | 20.802 | 20.968 | 31.853 | 1.00 80.38 | C |
| ATOM | 339 | CD | ARG | N | 579 | 19.487 | 20.222 | 31.726 | 1.00 84.49 | C |
| ATOM | 340 | NE | ARG | N | 579 | 18.438 | 21.069 | 31.147 | 1.00 88.84 | N |
| ATOM | 341 | CZ | ARG | N | 579 | 17.385 | 20.587 | 30.457 | 1.00 91.52 | C |

FIG. 5F

```
ATOM    342  NH1 ARG N 579      17.230  19.303  30.253  1.00 94.12           N
ATOM    343  NH2 ARG N 579      16.430  21.352  29.931  1.00 90.71           N
ATOM    344  H   ARG N 579      23.402  20.913  30.376  1.00  0.00           H
ATOM    345  HE  ARG N 579      18.509  22.039  31.265  1.00  0.00           H
ATOM    346 1HH1 ARG N 579      17.879  18.631  30.623  1.00  0.00           H
ATOM    347 2HH1 ARG N 579      16.423  18.975  29.754  1.00  0.00           H
ATOM    348 1HH2 ARG N 579      16.473  22.346  30.014  1.00  0.00           H
ATOM    349 2HH2 ARG N 579      15.675  20.923  29.427  1.00  0.00           H
ATOM    350  N   ILE N 580      25.362  19.713  32.371  1.00 79.12           N
ATOM    351  CA  ILE N 580      26.445  18.772  32.675  1.00 81.05           C
ATOM    352  C   ILE N 580      27.660  19.565  32.303  1.00 82.42           C
ATOM    353  O   ILE N 580      28.531  19.018  31.659  1.00 83.59           O
ATOM    354  CB  ILE N 580      26.246  17.503  31.784  1.00 80.80           C
ATOM    355  CG1 ILE N 580      25.193  16.697  32.429  1.00 84.04           C
ATOM    356  CG2 ILE N 580      27.451  16.589  31.650  1.00 78.88           C
ATOM    357  CD1 ILE N 580      24.516  16.191  31.215  1.00 86.00           C
ATOM    358  H   ILE N 580      25.445  20.241  31.548  1.00  0.00           H
ATOM    359  N   LEU N 581      27.698  20.865  32.557  1.00 83.28           N
ATOM    360  CA  LEU N 581      28.887  21.706  32.347  1.00 83.95           C
ATOM    361  C   LEU N 581      28.597  23.173  32.668  1.00 84.95           C
ATOM    362  O   LEU N 581      27.778  23.359  33.577  1.00 88.48           O
ATOM    363  CB  LEU N 581      29.461  21.581  30.920  1.00 82.81           C
ATOM    364  CG  LEU N 581      30.924  21.079  30.935  1.00 80.52           C
ATOM    365  CD1 LEU N 581      31.242  20.050  32.038  1.00 78.53           C
ATOM    366  CD2 LEU N 581      31.148  20.566  29.548  1.00 80.15           C
ATOM    367  H   LEU N 581      26.907  21.292  32.938  1.00  0.00           H
TER     368      LEU N 581
HETATM  369  C   ACE C   0      11.678  19.563  23.916  1.00 59.46           C
HETATM  370  O   ACE C   0      11.509  19.230  22.723  1.00 59.59           O
HETATM  371  CH3 ACE C   0      11.401  20.961  24.478  1.00 59.14           C
ATOM    372  N   TRP C 628      11.939  18.567  24.754  1.00 59.45           N
ATOM    373  CA  TRP C 628      12.345  17.262  24.249  1.00 58.85           C
ATOM    374  C   TRP C 628      11.305  16.438  23.468  1.00 59.28           C
ATOM    375  O   TRP C 628      11.646  15.639  22.589  1.00 59.31           O
ATOM    376  CB  TRP C 628      12.905  16.491  25.449  1.00 56.27           C
ATOM    377  CG  TRP C 628      14.324  16.987  25.710  1.00 55.28           C
ATOM    378  CD1 TRP C 628      14.560  17.945  26.654  1.00 52.77           C
ATOM    379  CD2 TRP C 628      15.466  16.576  25.059  1.00 52.52           C
ATOM    380  NE1 TRP C 628      15.852  18.149  26.605  1.00 53.20           N
ATOM    381  CE2 TRP C 628      16.442  17.360  25.680  1.00 53.25           C
ATOM    382  CE3 TRP C 628      15.833  15.676  24.060  1.00 49.19           C
ATOM    383  CZ2 TRP C 628      17.793  17.256  25.297  1.00 50.70           C
ATOM    384  CZ3 TRP C 628      17.180  15.570  23.699  1.00 49.98           C
ATOM    385  CH2 TRP C 628      18.158  15.350  24.304  1.00 47.48           C
ATOM    386  H   TRP C 628      11.881  18.708  25.724  1.00  0.00           H
ATOM    387  HE1 TRP C 628      16.338  18.759  27.208  1.00  0.00           H
ATOM    388  N   MET C 629       9.992  16.635  23.651  1.00 59.74           N
ATOM    389  CA  MET C 629       9.041  15.870  22.852  1.00 60.58           C
ATOM    390  C   MET C 629       8.978  16.434  21.441  1.00 59.92           C
ATOM    391  O   MET C 629       8.878  15.698  20.450  1.00 59.94           O
ATOM    392  CB  MET C 629       7.644  15.848  23.489  1.00 63.71           C
ATOM    393  CG  MET C 629       7.364  16.823  24.657  1.00 68.98           C
ATOM    394  SD  MET C 629       6.220  16.291  25.948  1.00 72.59           S
ATOM    395  CE  MET C 629       4.843  16.119  24.844  1.00 72.83           C
ATOM    396  H   MET C 629       9.728  17.227  24.356  1.00  0.00           H
ATOM    397  N   GLU C 630       9.151  17.749  21.302  1.00 59.19           N
ATOM    398  CA  GLU C 630       9.179  18.350  19.990  1.00 59.94           C
ATOM    399  C   GLU C 630      10.391  17.903  19.195  1.00 59.73           C
```

FIG. 5G

| ATOM | 400 | O | GLU | C | 630 | 10.317 | 17.666 | 17.988 | 1.00 | 58.71 | O |
|---|---|---|---|---|---|---|---|---|---|---|---|
| ATOM | 401 | CB | GLU | C | 630 | 9.192 | 19.876 | 20.063 | 1.00 | 62.30 | C |
| ATOM | 402 | CG | GLU | C | 630 | 9.263 | 20.558 | 18.693 | 1.00 | 66.55 | C |
| ATOM | 403 | CD | GLU | C | 630 | 8.214 | 20.271 | 17.616 | 1.00 | 69.57 | C |
| ATOM | 404 | OE1 | GLU | C | 630 | 7.325 | 19.430 | 17.788 | 1.00 | 71.12 | O |
| ATOM | 405 | OE2 | GLU | C | 630 | 8.304 | 20.921 | 16.577 | 1.00 | 71.20 | O |
| ATOM | 406 | H | GLU | C | 630 | 9.289 | 18.287 | 22.086 | 1.00 | 0.00 | H |
| ATOM | 407 | N | TRP | C | 631 | 11.517 | 17.795 | 19.893 | 1.00 | 60.09 | N |
| ATOM | 408 | CA | TRP | C | 631 | 12.758 | 17.353 | 19.309 | 1.00 | 60.33 | C |
| ATOM | 409 | C | TRP | C | 631 | 12.541 | 15.931 | 18.819 | 1.00 | 61.17 | C |
| ATOM | 410 | O | TRP | C | 631 | 12.869 | 15.598 | 17.708 | 1.00 | 61.33 | O |
| ATOM | 411 | CB | TRP | C | 631 | 13.836 | 17.478 | 20.395 | 1.00 | 56.29 | C |
| ATOM | 412 | CG | TRP | C | 631 | 15.206 | 16.925 | 19.960 | 1.00 | 54.47 | C |
| ATOM | 413 | CD1 | TRP | C | 631 | 16.103 | 17.708 | 19.291 | 1.00 | 54.11 | C |
| ATOM | 414 | CD2 | TRP | C | 631 | 15.644 | 15.637 | 20.169 | 1.00 | 50.58 | C |
| ATOM | 415 | NE1 | TRP | C | 631 | 17.137 | 16.928 | 19.120 | 1.00 | 53.39 | N |
| ATOM | 416 | CE2 | TRP | C | 631 | 16.924 | 15.687 | 19.621 | 1.00 | 50.81 | C |
| ATOM | 417 | CE3 | TRP | C | 631 | 15.169 | 14.490 | 20.782 | 1.00 | 44.66 | C |
| ATOM | 418 | CZ2 | TRP | C | 631 | 17.755 | 14.558 | 19.662 | 1.00 | 48.32 | C |
| ATOM | 419 | CZ3 | TRP | C | 631 | 15.995 | 13.360 | 20.809 | 1.00 | 45.04 | C |
| ATOM | 420 | CH2 | TRP | C | 631 | 17.274 | 13.377 | 20.242 | 1.00 | 45.24 | C |
| ATOM | 421 | H | TRP | C | 631 | 11.515 | 18.006 | 20.858 | 1.00 | 0.00 | H |
| ATOM | 422 | HE1 | TRP | C | 631 | 17.965 | 17.239 | 18.688 | 1.00 | 0.00 | H |
| ATOM | 423 | N | ASP | C | 632 | 11.873 | 15.089 | 19.562 | 1.00 | 62.54 | N |
| ATOM | 424 | CA | ASP | C | 632 | 11.600 | 13.733 | 19.160 | 1.00 | 64.59 | C |
| ATOM | 425 | C | ASP | C | 632 | 10.784 | 13.653 | 17.877 | 1.00 | 65.43 | C |
| ATOM | 426 | O | ASP | C | 632 | 11.049 | 12.839 | 16.989 | 1.00 | 65.87 | O |
| ATOM | 427 | CB | ASP | C | 632 | 10.801 | 13.059 | 20.184 | 1.00 | 66.75 | C |
| ATOM | 428 | CG | ASP | C | 632 | 11.553 | 11.867 | 20.759 | 1.00 | 70.81 | C |
| ATOM | 429 | OD1 | ASP | C | 632 | 11.763 | 10.875 | 20.036 | 1.00 | 73.19 | O |
| ATOM | 430 | OD2 | ASP | C | 632 | 11.864 | 12.009 | 21.934 | 1.00 | 73.17 | O |
| ATOM | 431 | H | ASP | C | 632 | 11.482 | 15.413 | 20.422 | 1.00 | 0.00 | H |
| ATOM | 432 | N | ARG | C | 633 | 9.741 | 14.481 | 17.788 | 1.00 | 65.95 | N |
| ATOM | 433 | CA | ARG | C | 633 | 8.846 | 14.452 | 16.645 | 1.00 | 66.10 | C |
| ATOM | 434 | C | ARG | C | 633 | 9.628 | 15.030 | 15.464 | 1.00 | 64.57 | C |
| ATOM | 435 | O | ARG | C | 633 | 9.583 | 14.449 | 14.377 | 1.00 | 64.74 | O |
| ATOM | 436 | CB | ARG | C | 633 | 7.586 | 15.329 | 16.804 | 1.00 | 70.93 | C |
| ATOM | 437 | CG | ARG | C | 633 | 6.473 | 15.063 | 17.832 | 1.00 | 77.51 | C |
| ATOM | 438 | CD | ARG | C | 633 | 5.742 | 16.383 | 18.096 | 1.00 | 83.59 | C |
| ATOM | 439 | NE | ARG | C | 633 | 5.101 | 16.320 | 19.404 | 1.00 | 90.92 | N |
| ATOM | 440 | CZ | ARG | C | 633 | 3.946 | 16.916 | 19.715 | 1.00 | 96.53 | C |
| ATOM | 441 | NH1 | ARG | C | 633 | 3.295 | 17.634 | 18.820 | 1.00 | 99.82 | N |
| ATOM | 442 | NH2 | ARG | C | 633 | 3.344 | 16.753 | 20.891 | 1.00 | 99.12 | N |
| ATOM | 443 | H | ARG | C | 633 | 9.604 | 15.123 | 18.523 | 1.00 | 0.00 | H |
| ATOM | 444 | HE | ARG | C | 633 | 5.536 | 15.785 | 20.096 | 1.00 | 0.00 | H |
| ATOM | 445 | 1HH1 | ARG | C | 633 | 3.715 | 17.801 | 17.918 | 1.00 | 0.00 | H |
| ATOM | 446 | 2HH1 | ARG | C | 633 | 2.486 | 18.174 | 19.079 | 1.00 | 0.00 | H |
| ATOM | 447 | 1HH2 | ARG | C | 633 | 3.713 | 16.130 | 21.573 | 1.00 | 0.00 | H |
| ATOM | 448 | 2HH2 | ARG | C | 633 | 2.491 | 17.256 | 21.077 | 1.00 | 0.00 | H |
| ATOM | 449 | N | GLU | C | 634 | 10.397 | 16.100 | 15.645 | 1.00 | 62.76 | N |
| ATOM | 450 | CA | GLU | C | 634 | 11.159 | 16.676 | 14.569 | 1.00 | 61.33 | C |
| ATOM | 451 | C | GLU | C | 634 | 12.229 | 15.727 | 14.081 | 1.00 | 60.46 | C |
| ATOM | 452 | O | GLU | C | 634 | 12.486 | 15.655 | 12.877 | 1.00 | 61.42 | O |
| ATOM | 453 | CB | GLU | C | 634 | 11.823 | 17.935 | 14.998 | 1.00 | 61.32 | C |
| ATOM | 454 | CG | GLU | C | 634 | 10.784 | 19.053 | 14.903 | 1.00 | 68.08 | C |
| ATOM | 455 | CD | GLU | C | 634 | 11.401 | 20.433 | 14.751 | 1.00 | 74.96 | C |
| ATOM | 456 | OE1 | GLU | C | 634 | 12.353 | 20.598 | 13.977 | 1.00 | 76.47 | O |
| ATOM | 457 | OE2 | GLU | C | 634 | 10.902 | 21.363 | 15.384 | 1.00 | 77.59 | O |

FIG. 5H

```
ATOM   458   H    GLU C 634     10.437  16.483  16.554  1.00  0.00           H
ATOM   459   N    ILE C 635     12.783  14.913  14.993  1.00 59.27           N
ATOM   460   CA   ILE C 635     13.782  13.906  14.663  1.00 56.77           C
ATOM   461   C    ILE C 635     13.110  12.816  13.854  1.00 57.26           C
ATOM   462   O    ILE C 635     13.714  12.292  12.927  1.00 56.53           O
ATOM   463   CB   ILE C 635     14.429  13.299  15.953  1.00 52.95           C
ATOM   464   CG1  ILE C 635     15.236  14.321  16.698  1.00 47.91           C
ATOM   465   CG2  ILE C 635     15.388  12.182  15.569  1.00 52.10           C
ATOM   466   CD1  ILE C 635     16.358  14.961  15.927  1.00 50.08           C
ATOM   467   H    ILE C 635     12.540  15.067  15.936  1.00  0.00           H
ATOM   468   N    ASN C 636     11.854  12.452  14.086  1.00 58.11           N
ATOM   469   CA   ASN C 636     11.273  11.345  13.347  1.00 58.91           C
ATOM   470   C    ASN C 636     10.775  11.849  12.030  1.00 59.34           C
ATOM   471   O    ASN C 636     10.926  11.176  11.020  1.00 59.71           O
ATOM   472   CB   ASN C 636     10.132  10.719  14.134  1.00 59.74           C
ATOM   473   CG   ASN C 636     10.632  10.044  15.400  1.00 61.95           C
ATOM   474   OD1  ASN C 636     11.698   9.427  15.428  1.00 65.00           O
ATOM   475   ND2  ASN C 636      9.938  10.198  16.516  1.00 60.78           N
ATOM   476   H    ASN C 636     11.345  12.892  14.807  1.00  0.00           H
ATOM   477  1HD2  ASN C 636     10.323   9.834  17.341  1.00  0.00           H
ATOM   478  2HD2  ASN C 636      9.118  10.706  16.495  1.00  0.00           H
ATOM   479   N    ASN C 637     10.278  13.076  12.015  1.00 59.84           N
ATOM   480   CA   ASN C 637      9.779  13.751  10.816  1.00 61.12           C
ATOM   481   C    ASN C 637     10.634  13.839   9.723  1.00 61.25           C
ATOM   482   O    ASN C 637     10.585  13.594   8.538  1.00 61.53           O
ATOM   483   CB   ASN C 637      9.383  15.219  11.029  1.00 64.01           C
ATOM   484   CG   ASN C 637      8.112  15.513  11.887  1.00 67.80           C
ATOM   485   OD1  ASN C 637      7.302  14.605  12.111  1.00 68.43           O
ATOM   486   ND2  ASN C 637      7.948  16.748  12.355  1.00 68.62           N
ATOM   487   H    ASN C 637     10.230  13.350  12.877  1.00  0.00           H
ATOM   488  1HD2  ASN C 637      7.144  16.914  12.846  1.00  0.00           H
ATOM   489  2HD2  ASN C 637      8.650  17.412  12.187  1.00  0.00           H
ATOM   490   N    TYR C 638     12.033  14.300  10.102  1.00 60.30           N
ATOM   491   CA   TYR C 638     13.127  14.392   9.169  1.00 58.95           C
ATOM   492   C    TYR C 638     13.679  13.029   8.854  1.00 58.12           C
ATOM   493   O    TYR C 638     14.008  12.788   7.698  1.00 58.25           O
ATOM   494   CB   TYR C 638     14.165  15.327   9.774  1.00 58.34           C
ATOM   495   CG   TYR C 638     13.667  16.749   9.673  1.00 58.76           C
ATOM   496   CD1  TYR C 638     13.303  17.225   8.418  1.00 59.13           C
ATOM   497   CD2  TYR C 638     13.521  17.567  10.800  1.00 59.56           C
ATOM   498   CE1  TYR C 638     12.850  18.517   8.256  1.00 58.59           C
ATOM   499   CE2  TYR C 638     13.091  18.900  10.637  1.00 60.72           C
ATOM   500   CZ   TYR C 638     12.738  19.343   9.354  1.00 59.43           C
ATOM   501   OH   TYR C 638     12.451  20.666   9.088  1.00 58.81           O
ATOM   502   H    TYR C 638     12.162  14.682  11.009  1.00  0.00           H
ATOM   503   HH   TYR C 638     12.351  20.876   8.165  1.00  0.00           H
ATOM   504   N    THR C 639     13.706  12.108   9.796  1.00 57.10           N
ATOM   505   CA   THR C 639     14.134  10.771   9.461  1.00 57.84           C
ATOM   506   C    THR C 639     13.232  10.085   8.424  1.00 58.82           C
ATOM   507   O    THR C 639     13.725   9.331   7.554  1.00 58.69           O
ATOM   508   CB   THR C 639     14.163   9.904  10.683  1.00 57.69           C
ATOM   509   OG1  THR C 639     15.110  10.474  11.544  1.00 60.10           O
ATOM   510   CG2  THR C 639     14.597   8.478  10.387  1.00 55.45           C
ATOM   511   H    THR C 639     13.402  12.348  10.690  1.00  0.00           H
ATOM   512   HG1  THR C 639     14.818  11.323  11.889  1.00  0.00           H
ATOM   513   N    SER C 640     11.916  10.315   8.505  1.00 59.42           N
ATOM   514   CA   SER C 640     10.997   9.745   7.531  1.00 60.07           C
ATOM   515   C    SER C 640     11.177  10.391   6.160  1.00 58.97           C
```

FIG. 5I

```
ATOM    516  O   SER C 640      11.169   9.642   5.177  1.00 60.33           O
ATOM    517  CB  SER C 640       9.549   9.934   7.966  1.00 62.43           C
ATOM    518  OG  SER C 640       9.343   9.238   9.188  1.00 69.53           O
ATOM    519  H   SER C 640      11.544  10.854   9.240  1.00  0.00           H
ATOM    520  HG  SER C 640       9.444   9.098   9.074  1.00  0.00           H
ATOM    521  N   LEU C 641      11.375  11.710   6.057  1.00 56.88           N
ATOM    522  CA  LEU C 641      11.619  12.351   4.785  1.00 55.95           C
ATOM    523  C   LEU C 641      12.948  11.832   4.190  1.00 56.33           C
ATOM    524  O   LEU C 641      13.039  11.552   3.988  1.00 55.67           O
ATOM    525  CB  LEU C 641      11.658  13.879   5.008  1.00 53.81           C
ATOM    526  CG  LEU C 641      11.718  14.767   3.765  1.00 52.82           C
ATOM    527  CD1 LEU C 641      10.375  14.703   3.035  1.00 52.33           C
ATOM    528  CD2 LEU C 641      12.047  16.198   4.163  1.00 50.59           C
ATOM    529  H   LEU C 641      11.357  12.252   6.875  1.00  0.00           H
ATOM    530  N   ILE C 642      13.988  11.612   5.019  1.00 55.99           N
ATOM    531  CA  ILE C 642      15.290  11.153   4.549  1.00 55.40           C
ATOM    532  C   ILE C 642      15.163   9.729   4.112  1.00 55.08           C
ATOM    533  O   ILE C 642      15.740   9.343   3.115  1.00 55.36           O
ATOM    534  CB  ILE C 642      16.384  11.240   5.647  1.00 54.86           C
ATOM    535  CG1 ILE C 642      16.630  12.661   6.041  1.00 53.06           C
ATOM    536  CG2 ILE C 642      17.722  10.778   5.097  1.00 57.37           C
ATOM    537  CD1 ILE C 642      17.490  12.825   7.287  1.00 48.58           C
ATOM    538  H   ILE C 642      13.884  11.813   5.990  1.00  0.00           H
ATOM    539  N   HIS C 643      14.415   8.904   4.785  1.00 55.14           N
ATOM    540  CA  HIS C 643      14.197   7.568   4.350  1.00 56.94           C
ATOM    541  C   HIS C 643      13.527   7.513   2.940  1.00 55.82           C
ATOM    542  O   HIS C 643      13.928   6.699   2.100  1.00 55.49           O
ATOM    543  CB  HIS C 643      13.347   6.771   5.191  1.00 63.78           C
ATOM    544  CG  HIS C 643      14.340   6.051   6.098  1.00 73.07           C
ATOM    545  ND1 HIS C 643      14.544   4.739   6.144  1.00 78.26           N
ATOM    546  CD2 HIS C 643      15.193   6.704   6.938  1.00 77.77           C
ATOM    547  CE1 HIS C 643      15.501   4.583   6.998  1.00 81.50           C
ATOM    548  NE2 HIS C 643      15.895   5.758   7.471  1.00 81.84           N
ATOM    549  H   HIS C 643      13.952   9.336   5.596  1.00  0.00           H
ATOM    550  HD1 HIS C 643      14.017   4.059   5.688  1.00  0.00           H
ATOM    551  HE2 HIS C 643      16.617   5.921   8.100  1.00  0.00           H
ATOM    552  N   SER C 644      12.503   8.344   2.761  1.00 55.58           N
ATOM    553  CA  SER C 644      11.826   8.384   1.478  1.00 54.97           C
ATOM    554  C   SER C 644      12.782   8.888   0.398  1.00 53.50           C
ATOM    555  O   SER C 644      12.797   8.293  -0.691  1.00 53.52           O
ATOM    556  CB  SER C 644      10.644   9.369   1.377  1.00 56.29           C
ATOM    557  OG  SER C 644       9.823   9.759   2.572  1.00 59.92           O
ATOM    558  H   SER C 644      12.128   8.851   3.524  1.00  0.00           H
ATOM    559  HG  SER C 644       9.441   8.970   2.959  1.00  0.00           H
ATOM    560  N   LEU C 645      13.613   9.918   0.673  1.00 51.33           N
ATOM    561  CA  LEU C 645      14.485  10.438  -0.351  1.00 48.71           C
ATOM    562  C   LEU C 645      15.593   9.476  -0.651  1.00 49.35           C
ATOM    563  O   LEU C 645      15.914   9.318  -1.820  1.00 49.33           O
ATOM    564  CB  LEU C 645      15.027  11.807   0.080  1.00 45.58           C
ATOM    565  CG  LEU C 645      13.979  12.903   0.305  1.00 39.61           C
ATOM    566  CD1 LEU C 645      14.665  14.149   0.710  1.00 41.30           C
ATOM    567  CD2 LEU C 645      13.200  13.183  -0.954  1.00 38.15           C
ATOM    568  H   LEU C 645      13.620  10.325   1.566  1.00  0.00           H
ATOM    569  N   ILE C 646      16.114   8.734   0.334  1.00 48.24           N
ATOM    570  CA  ILE C 646      17.178   7.748   0.106  1.00 48.80           C
ATOM    571  C   ILE C 646      16.595   6.620  -0.736  1.00 51.17           C
ATOM    572  O   ILE C 646      17.236   6.140  -1.676  1.00 50.43           O
ATOM    573  CB  ILE C 646      17.720   7.222   1.450  1.00 44.77           C
```

FIG. 5J

```
ATOM    574  CG1 ILE C 646      18.414    8.325    2.218  1.00 43.19           C
ATOM    575  CG2 ILE C 646      18.745    6.158    1.182  1.00 43.97           C
ATOM    576  CD1 ILE C 646      18.854    7.897    3.621  1.00 39.46           C
ATOM    577  H   ILE C 646      15.785    8.879    1.246  1.00  0.00           H
ATOM    578  N   GLU C 647      15.348    6.236   -0.482  1.00 54.35           N
ATOM    579  CA  GLU C 647      14.685    5.186   -1.244  1.00 56.99           C
ATOM    580  C   GLU C 647      14.377    5.647   -2.682  1.00 57.37           C
ATOM    581  O   GLU C 647      14.604    4.923   -3.662  1.00 58.06           O
ATOM    582  CB  GLU C 647      13.408    4.828   -0.527  1.00 62.05           C
ATOM    583  CG  GLU C 647      12.691    3.564   -1.047  1.00 71.88           C
ATOM    584  CD  GLU C 647      11.372    3.218   -0.346  1.00 79.96           C
ATOM    585  OE1 GLU C 647      10.947    3.931    0.578  1.00 83.26           O
ATOM    586  OE2 GLU C 647      10.766    2.217   -0.738  1.00 83.60           O
ATOM    587  H   GLU C 647      14.843    6.711    0.208  1.00  0.00           H
ATOM    588  N   GLU C 648      13.876    6.871   -2.874  1.00 57.16           N
ATOM    589  CA  GLU C 648      13.588    7.431   -4.178  1.00 57.13           C
ATOM    590  C   GLU C 648      14.863    7.517   -4.984  1.00 55.73           C
ATOM    591  O   GLU C 648      14.864    7.188   -6.175  1.00 55.55           O
ATOM    592  CB  GLU C 648      13.051    8.796   -4.039  1.00 62.05           C
ATOM    593  CG  GLU C 648      12.503    9.437   -5.318  1.00 74.11           C
ATOM    594  CD  GLU C 648      11.969   10.872   -5.126  1.00 85.94           C
ATOM    595  OE1 GLU C 648      11.991   11.409   -4.008  1.00 91.79           O
ATOM    596  OE2 GLU C 648      11.521   11.471   -6.110  1.00 88.20           O
ATOM    597  H   GLU C 648      13.711    7.409   -2.074  1.00  0.00           H
ATOM    598  N   SER C 649      15.950    7.961   -4.364  1.00 54.84           N
ATOM    599  CA  SER C 649      17.251    8.032   -4.994  1.00 53.47           C
ATOM    600  C   SER C 649      17.811    6.694   -5.403  1.00 53.80           C
ATOM    601  O   SER C 649      18.368    6.564   -6.482  1.00 53.07           O
ATOM    602  CB  SER C 649      18.191    8.704   -4.055  1.00 52.08           C
ATOM    603  OG  SER C 649      17.841   10.043   -3.742  1.00 48.93           O
ATOM    604  H   SER C 649      15.881    8.274   -3.436  1.00  0.00           H
ATOM    605  HG  SER C 649      17.888   10.547   -4.561  1.00  0.00           H
ATOM    606  N   GLN C 650      17.622    5.684   -4.563  1.00 52.79           N
ATOM    607  CA  GLN C 650      17.985    4.285   -4.808  1.00 52.64           C
ATOM    608  C   GLN C 650      17.303    3.776   -6.071  1.00 53.04           C
ATOM    609  O   GLN C 650      17.951    3.085   -6.882  1.00 54.05           O
ATOM    610  CB  GLN C 650      17.547    3.387   -3.634  1.00 56.65           C
ATOM    611  CG  GLN C 650      18.565    2.745   -2.685  1.00 62.17           C
ATOM    612  CD  GLN C 650      17.982    2.264   -1.334  1.00 66.79           C
ATOM    613  OE1 GLN C 650      16.991    1.535   -1.224  1.00 69.78           O
ATOM    614  NE2 GLN C 650      18.538    2.637   -0.192  1.00 67.82           N
ATOM    615  H   GLN C 650      17.260    5.899   -3.670  1.00  0.00           H
ATOM    616 1HE2 GLN C 650      18.083    2.295    0.609  1.00  0.00           H
ATOM    617 2HE2 GLN C 650      19.324    3.204   -0.193  1.00  0.00           H
ATOM    618  N   ASN C 651      16.035    4.183   -6.268  1.00 51.27           N
ATOM    619  CA  ASN C 651      15.261    3.761   -7.435  1.00 49.91           C
ATOM    620  C   ASN C 651      15.708    4.500   -8.681  1.00 48.34           C
ATOM    621  O   ASN C 651      15.988    3.912   -9.726  1.00 47.51           O
ATOM    622  CB  ASN C 651      13.776    4.018   -7.246  1.00 49.79           C
ATOM    623  CG  ASN C 651      13.276    3.154   -6.125  1.00 53.41           C
ATOM    624  OD1 ASN C 651      13.709    2.010   -5.961  1.00 52.64           O
ATOM    625  ND2 ASN C 651      12.418    3.728   -5.276  1.00 59.61           N
ATOM    626  H   ASN C 651      15.627    4.783   -5.608  1.00  0.00           H
ATOM    627 1HD2 ASN C 651      12.154    3.212   -4.475  1.00  0.00           H
ATOM    628 2HD2 ASN C 651      12.157    4.647   -5.399  1.00  0.00           H
ATOM    629  N   GLN C 652      15.864    5.821   -8.587  1.00 47.33           N
ATOM    630  CA  GLN C 652      16.350    6.623   -9.690  1.00 47.23           C
ATOM    631  C   GLN C 652      17.758    6.187  -10.002  1.00 47.47           C
```

FIG. 5K

```
ATOM  632  O    GLN C 652      18.093   6.195 -11.164  1.00 48.04           O
ATOM  633  CB   GLN C 652      16.307   8.040  -9.279  1.00 45.56           C
ATOM  634  CG   GLN C 652      16.453   9.174 -10.302  1.00 47.99           C
ATOM  635  CD   GLN C 652      15.382   9.271 -11.366  1.00 51.30           C
ATOM  636  OE1  GLN C 652      14.275   9.750 -11.134  1.00 51.42           O
ATOM  637  NE2  GLN C 652      15.688   8.915 -12.603  1.00 47.15           N
ATOM  638  H    GLN C 652      15.598   6.247  -7.749  1.00  0.00           H
ATOM  639  1HE2 GLN C 652      14.985   8.988 -13.303  1.00  0.00           H
ATOM  640  2HE2 GLN C 652      16.588   8.582 -12.832  1.00  0.00           H
ATOM  641  N    GLN C 653      18.596   5.741  -9.080  1.00 47.45           N
ATOM  642  CA   GLN C 653      19.926   5.262  -9.403  1.00 49.03           C
ATOM  643  C    GLN C 653      19.851   4.058 -10.322  1.00 51.89           C
ATOM  644  O    GLN C 653      20.554   4.029 -11.335  1.00 52.35           O
ATOM  645  CB   GLN C 653      20.669   4.856  -8.157  1.00 47.54           C
ATOM  646  CG   GLN C 653      22.164   4.660  -8.449  1.00 46.28           C
ATOM  647  CD   GLN C 653      22.929   5.903  -8.922  1.00 45.38           C
ATOM  648  OE1  GLN C 653      22.474   7.036  -8.956  1.00 45.74           O
ATOM  649  NE2  GLN C 653      24.191   5.913  -9.220  1.00 45.80           N
ATOM  650  H    GLN C 653      18.285   5.717  -8.155  1.00  0.00           H
ATOM  651  1HE2 GLN C 653      24.602   6.803  -9.348  1.00  0.00           H
ATOM  652  2HE2 GLN C 653      24.738   5.108  -9.124  1.00  0.00           H
ATOM  653  N    GLU C 654      18.952   3.102 -10.025  1.00 54.43           N
ATOM  654  CA   GLU C 654      18.763   1.932 -10.883  1.00 55.77           C
ATOM  655  C    GLU C 654      18.222   2.339 -12.253  1.00 55.11           C
ATOM  656  O    GLU C 654      18.762   1.915 -13.285  1.00 55.24           O
ATOM  657  CB   GLU C 654      17.815   0.928 -10.199  1.00 59.12           C
ATOM  658  CG   GLU C 654      18.515   0.035  -9.155  1.00 69.14           C
ATOM  659  CD   GLU C 654      17.642  -0.522  -8.002  1.00 76.48           C
ATOM  660  OE1  GLU C 654      17.220   0.245  -7.134  1.00 77.99           O
ATOM  661  OE2  GLU C 654      17.376  -1.728  -7.946  1.00 78.90           O
ATOM  662  H    GLU C 654      18.388   3.228  -9.231  1.00  0.00           H
ATOM  663  N    LYS C 655      17.219   3.226 -12.313  1.00 54.37           N
ATOM  664  CA   LYS C 655      16.635   3.697 -13.564  1.00 54.47           C
ATOM  665  C    LYS C 655      17.643   4.441 -14.445  1.00 54.88           C
ATOM  666  O    LYS C 655      17.713   4.286 -15.665  1.00 54.37           O
ATOM  667  CB   LYS C 655      15.456   4.583 -13.204  1.00 54.89           C
ATOM  668  CG   LYS C 655      14.495   4.868 -14.361  1.00 59.61           C
ATOM  669  CD   LYS C 655      13.201   5.577 -13.910  1.00 65.23           C
ATOM  670  CE   LYS C 655      12.251   4.748 -13.002  1.00 68.13           C
ATOM  671  NZ   LYS C 655      10.937   5.360 -12.806  1.00 69.83           N
ATOM  672  H    LYS C 655      16.858   3.551 -11.458  1.00  0.00           H
ATOM  673  1HZ  LYS C 655      11.029   6.298 -12.366  1.00  0.00           H
ATOM  674  2HZ  LYS C 655      10.454   5.475 -13.724  1.00  0.00           H
ATOM  675  3HZ  LYS C 655      10.344   4.756 -12.200  1.00  0.00           H
ATOM  676  N    ASN C 656      18.474   5.275 -13.838  1.00 56.18           N
ATOM  677  CA   ASN C 656      19.463   6.063 -14.534  1.00 56.44           C
ATOM  678  C    ASN C 656      20.510   5.128 -15.026  1.00 57.72           C
ATOM  679  O    ASN C 656      20.860   5.283 -16.194  1.00 58.23           O
ATOM  680  CB   ASN C 656      20.117   7.094 -13.615  1.00 56.38           C
ATOM  681  CG   ASN C 656      19.142   8.214 -13.246  1.00 57.60           C
ATOM  682  OD1  ASN C 656      18.270   8.618 -14.035  1.00 59.08           O
ATOM  683  ND2  ASN C 656      19.141   8.698 -12.009  1.00 57.31           N
ATOM  684  H    ASN C 656      18.353   5.436 -12.874  1.00  0.00           H
ATOM  685  1HD2 ASN C 656      18.438   9.305 -11.726  1.00  0.00           H
ATOM  686  2HD2 ASN C 656      19.787   8.297 -11.386  1.00  0.00           H
ATOM  687  N    GLU C 657      20.960   4.129 -14.248  1.00 58.95           N
ATOM  688  CA   GLU C 657      21.918   3.154 -14.752  1.00 61.26           C
ATOM  689  C    GLU C 657      21.326   2.381 -15.914  1.00 62.47           C
```

FIG. 5L

| | | | | | | | | | |
|---|---|---|---|---|---|---|---|---|---|
| ATOM | 690 | O | GLU | C 657 | 21.999 | 2.178 | -16.920 | 1.00 62.52 | O |
| ATOM | 691 | CB | GLU | C 657 | 22.297 | 2.184 | -13.687 | 1.00 62.42 | C |
| ATOM | 692 | CG | GLU | C 657 | 23.051 | 2.811 | -12.514 | 1.00 65.99 | C |
| ATOM | 693 | CD | GLU | C 657 | 23.410 | 1.852 | -11.389 | 1.00 68.51 | C |
| ATOM | 694 | OE1 | GLU | C 657 | 23.152 | 0.650 | -11.481 | 1.00 72.44 | O |
| ATOM | 695 | OE2 | GLU | C 657 | 23.970 | 2.322 | -10.407 | 1.00 69.49 | O |
| ATOM | 696 | H | GLU | C 657 | 20.656 | 4.056 | -13.317 | 1.00 0.00 | H |
| ATOM | 697 | N | GLN | C 658 | 20.051 | 1.999 | -15.851 | 1.00 63.77 | N |
| ATOM | 698 | CA | GLN | C 658 | 19.379 | 1.342 | -16.972 | 1.00 64.97 | C |
| ATOM | 699 | C | GLN | C 658 | 19.373 | 2.235 | -18.211 | 1.00 64.88 | C |
| ATOM | 700 | O | GLN | C 658 | 19.620 | 1.701 | -19.282 | 1.00 64.89 | O |
| ATOM | 701 | CB | GLN | C 658 | 17.908 | 1.040 | -16.710 | 1.00 67.79 | C |
| ATOM | 702 | CG | GLN | C 658 | 17.473 | 0.109 | -15.580 | 1.00 69.56 | C |
| ATOM | 703 | CD | GLN | C 658 | 15.981 | 0.184 | -15.253 | 1.00 71.90 | C |
| ATOM | 704 | OE1 | GLN | C 658 | 15.214 | 1.130 | -15.491 | 1.00 69.19 | O |
| ATOM | 705 | NE2 | GLN | C 658 | 15.580 | -0.892 | -14.597 | 1.00 73.46 | N |
| ATOM | 706 | H | GLN | C 658 | 19.527 | 2.154 | -15.036 | 1.00 0.00 | H |
| ATOM | 707 | 1HE2 | GLN | C 658 | 14.637 | -0.917 | -14.331 | 1.00 0.00 | H |
| ATOM | 708 | 2HE2 | GLN | C 658 | 16.241 | -1.579 | -14.383 | 1.00 0.00 | H |
| ATOM | 709 | N | GLU | C 659 | 19.099 | 3.533 | -18.086 | 1.00 64.42 | N |
| ATOM | 710 | CA | GLU | C 659 | 19.001 | 4.408 | -19.239 | 1.00 64.32 | C |
| ATOM | 711 | C | GLU | C 659 | 20.328 | 4.664 | -19.917 | 1.00 62.40 | C |
| ATOM | 712 | O | GLU | C 659 | 20.389 | 5.040 | -21.080 | 1.00 61.69 | O |
| ATOM | 713 | CB | GLU | C 659 | 18.413 | 5.726 | -18.809 | 1.00 68.95 | C |
| ATOM | 714 | CG | GLU | C 659 | 18.001 | 6.640 | -19.976 | 1.00 78.11 | C |
| ATOM | 715 | CD | GLU | C 659 | 17.379 | 7.956 | -19.530 | 1.00 86.51 | C |
| ATOM | 716 | OE1 | GLU | C 659 | 17.214 | 8.159 | -18.321 | 1.00 90.49 | O |
| ATOM | 717 | OE2 | GLU | C 659 | 17.049 | 8.781 | -20.388 | 1.00 90.41 | O |
| ATOM | 718 | H | GLU | C 659 | 18.930 | 3.898 | -17.190 | 1.00 0.00 | H |
| ATOM | 719 | N | LEU | C 660 | 21.374 | 4.592 | -19.120 | 1.00 61.04 | N |
| ATOM | 720 | CA | LEU | C 660 | 22.691 | 4.691 | -19.683 | 1.00 60.69 | C |
| ATOM | 721 | C | LEU | C 660 | 23.036 | 3.531 | -20.613 | 1.00 60.42 | C |
| ATOM | 722 | O | LEU | C 660 | 23.705 | 3.774 | -21.615 | 1.00 60.27 | O |
| ATOM | 723 | CB | LEU | C 660 | 23.697 | 4.805 | -18.521 | 1.00 60.36 | C |
| ATOM | 724 | CG | LEU | C 660 | 24.642 | 6.019 | -18.618 | 1.00 59.86 | C |
| ATOM | 725 | CD1 | LEU | C 660 | 23.883 | 7.314 | -18.999 | 1.00 64.42 | C |
| ATOM | 726 | CD2 | LEU | C 660 | 25.334 | 6.131 | -17.317 | 1.00 55.37 | C |
| ATOM | 727 | H | LEU | C 660 | 21.231 | 4.584 | -18.144 | 1.00 0.00 | H |
| ATOM | 728 | N | LEU | C 661 | 22.575 | 2.323 | -20.325 | 1.00 60.33 | N |
| ATOM | 729 | CA | LEU | C 661 | 22.856 | 1.140 | -21.141 | 1.00 60.95 | C |
| ATOM | 730 | C | LEU | C 661 | 22.049 | 0.974 | -22.446 | 1.00 61.99 | C |
| ATOM | 731 | O | LEU | C 661 | 20.871 | 1.318 | -22.502 | 1.00 60.13 | O |
| ATOM | 732 | CB | LEU | C 661 | 22.646 | -0.115 | -20.264 | 1.00 59.85 | C |
| ATOM | 733 | CG | LEU | C 661 | 23.452 | -0.260 | -18.988 | 1.00 57.97 | C |
| ATOM | 734 | CD1 | LEU | C 661 | 23.106 | -1.535 | -18.261 | 1.00 57.79 | C |
| ATOM | 735 | CD2 | LEU | C 661 | 24.896 | -0.304 | -19.360 | 1.00 54.71 | C |
| ATOM | 736 | H | LEU | C 661 | 21.881 | 2.223 | -19.630 | 1.00 0.00 | H |
| TER | 737 | | LEU | C 661 | | | | | |
| HETATM | 738 | O | HOH | 1 | 20.374 | 11.213 | -18.121 | 1.00 71.66 | O |
| HETATM | 739 | 1H | HOH | 1 | 20.431 | 10.325 | -18.535 | 1.00 0.00 | H |
| HETATM | 740 | 2H | HOH | 1 | 19.472 | 11.248 | -17.822 | 1.00 0.00 | H |
| HETATM | 741 | O | HOH | 2 | 21.271 | 8.706 | -17.797 | 1.00 41.79 | O |
| HETATM | 742 | 1H | HOH | 2 | 21.310 | 7.838 | -17.376 | 1.00 0.00 | H |
| HETATM | 743 | 2H | HOH | 2 | 22.207 | 8.971 | -17.787 | 1.00 0.00 | H |
| HETATM | 744 | O | HOH | 3 | 20.650 | 1.729 | -6.022 | 1.00 46.90 | O |
| HETATM | 745 | 1H | HOH | 3 | 19.744 | 1.986 | -6.245 | 1.00 0.00 | H |
| HETATM | 746 | 2H | HOH | 3 | 21.074 | 2.571 | -5.777 | 1.00 0.00 | H |
| HETATM | 747 | O | HOH | 4 | 22.303 | 1.121 | -8.408 | 1.00 60.62 | O |

FIG. 5M

| | | | | | | | | | |
|---|---|---|---|---|---|---|---|---|---|
| HETATM | 748 | 1H | HOH | 4 | 22.825 | 1.923 | -8.306 | 1.00 | 0.00 | H |
| HETATM | 749 | 2H | HOH | 4 | 21.811 | 1.091 | -7.565 | 1.00 | 0.00 | H |
| HETATM | 750 | O | HOH | 5 | 12.657 | 5.253 | 8.200 | 1.00 | 56.12 | O |
| HETATM | 751 | 1H | HOH | 5 | 12.382 | 4.344 | 8.353 | 1.00 | 0.00 | H |
| HETATM | 752 | 2H | HOH | 5 | 11.869 | 5.752 | 8.457 | 1.00 | 0.00 | H |
| HETATM | 753 | O | HOH | 6 | 9.078 | 18.813 | 26.094 | 1.00 | 49.33 | O |
| HETATM | 754 | 1H | HOH | 6 | 9.131 | 17.970 | 25.664 | 1.00 | 0.00 | H |
| HETATM | 755 | 2H | HOH | 6 | 9.244 | 19.463 | 25.419 | 1.00 | 0.00 | H |
| HETATM | 756 | O | HOH | 7 | 7.670 | 21.185 | 11.788 | 1.00 | 53.95 | O |
| HETATM | 757 | 1H | HOH | 7 | 7.025 | 21.036 | 12.470 | 1.00 | 0.00 | H |
| HETATM | 758 | 2H | HOH | 7 | 8.510 | 21.265 | 12.230 | 1.00 | 0.00 | H |
| HETATM | 759 | O | HOH | 8 | 8.303 | 19.620 | 23.607 | 1.00 | 92.51 | O |
| HETATM | 760 | 1H | HOH | 8 | 8.399 | 18.988 | 22.917 | 1.00 | 0.00 | H |
| HETATM | 761 | 2H | HOH | 8 | 9.047 | 20.193 | 23.630 | 1.00 | 0.00 | H |
| HETATM | 762 | O | HOH | 9 | 14.426 | 18.177 | 16.971 | 1.00 | 91.64 | O |
| HETATM | 763 | 1H | HOH | 9 | 15.010 | 18.890 | 16.831 | 1.00 | 0.00 | H |
| HETATM | 764 | 2H | HOH | 9 | 13.573 | 18.570 | 17.105 | 1.00 | 0.00 | H |
| HETATM | 765 | O | HOH | 10 | 6.660 | 18.291 | 14.901 | 1.00 | 47.78 | O |
| HETATM | 766 | 1H | HOH | 10 | 6.912 | 18.615 | 14.042 | 1.00 | 0.00 | H |
| HETATM | 767 | 2H | HOH | 10 | 7.036 | 18.893 | 15.527 | 1.00 | 0.00 | H |
| HETATM | 768 | O | HOH | 11 | 9.801 | 17.869 | 7.746 | 1.00 | 50.95 | O |
| HETATM | 769 | 1H | HOH | 11 | 9.411 | 16.994 | 7.627 | 1.00 | 0.00 | H |
| HETATM | 770 | 2H | HOH | 11 | 10.574 | 17.739 | 8.259 | 1.00 | 0.00 | H |
| HETATM | 771 | O | HOH | 12 | 7.790 | 15.753 | 8.005 | 1.00 | 53.41 | O |
| HETATM | 772 | 1H | HOH | 12 | 7.613 | 15.541 | 8.927 | 1.00 | 0.00 | H |
| HETATM | 773 | 2H | HOH | 12 | 8.562 | 15.235 | 7.778 | 1.00 | 0.00 | H |
| HETATM | 774 | O | HOH | 13 | 14.145 | 18.206 | 2.097 | 1.00 | 57.88 | O |
| HETATM | 775 | 1H | HOH | 13 | 14.620 | 17.400 | 2.306 | 1.00 | 0.00 | H |
| HETATM | 776 | 2H | HOH | 13 | 13.390 | 18.116 | 2.522 | 1.00 | 0.00 | H |
| HETATM | 777 | O | HOH | 14 | 12.314 | 6.447 | -8.867 | 1.00 | 65.60 | O |
| HETATM | 778 | 1H | HOH | 14 | 12.737 | 7.223 | -9.273 | 1.00 | 0.00 | H |
| HETATM | 779 | 2H | HOH | 14 | 12.746 | 6.378 | -8.026 | 1.00 | 0.00 | H |
| HETATM | 780 | O | HOH | 15 | 21.545 | -1.804 | -13.790 | 1.00 | 49.07 | O |
| HETATM | 781 | 1H | HOH | 15 | 21.496 | -2.647 | -14.243 | 1.00 | 0.00 | H |
| HETATM | 782 | 2H | HOH | 15 | 20.714 | -1.364 | -13.979 | 1.00 | 0.00 | H |
| HETATM | 783 | O | HOH | 16 | 22.569 | 8.158 | -11.409 | 1.00 | 46.71 | O |
| HETATM | 784 | 1H | HOH | 16 | 22.403 | 7.556 | -10.690 | 1.00 | 0.00 | H |
| HETATM | 785 | 2H | HOH | 16 | 22.970 | 8.920 | -10.966 | 1.00 | 0.00 | H |
| HETATM | 786 | O | HOH | 17 | 15.788 | 9.728 | -7.160 | 1.00 | 65.57 | O |
| HETATM | 787 | 1H | HOH | 17 | 16.729 | 9.881 | -7.059 | 1.00 | 0.00 | H |
| HETATM | 788 | 2H | HOH | 17 | 15.600 | 8.894 | -6.726 | 1.00 | 0.00 | H |
| HETATM | 789 | O | HOH | 18 | 7.205 | 11.385 | 12.307 | 1.00 | 55.74 | O |
| HETATM | 790 | 1H | HOH | 18 | 8.081 | 11.402 | 11.900 | 1.00 | 0.00 | H |
| HETATM | 791 | 2H | HOH | 18 | 6.937 | 12.318 | 12.282 | 1.00 | 0.00 | H |
| HETATM | 792 | O | HOH | 19 | 9.847 | 10.295 | -2.390 | 1.00 | 36.62 | O |
| HETATM | 793 | 1H | HOH | 19 | 8.917 | 10.375 | -2.193 | 1.00 | 0.00 | H |
| HETATM | 794 | 2H | HOH | 19 | 10.216 | 9.724 | -1.732 | 1.00 | 0.00 | H |
| HETATM | 795 | O | HOH | 20 | 14.009 | 23.313 | 28.896 | 1.00 | 73.77 | O |
| HETATM | 796 | 1H | HOH | 20 | 14.838 | 23.163 | 28.435 | 1.00 | 0.00 | H |
| HETATM | 797 | 2H | HOH | 20 | 13.892 | 22.574 | 29.472 | 1.00 | 0.00 | H |
| HETATM | 798 | O | HOH | 21 | 13.472 | 10.407 | -8.621 | 1.00 | 45.61 | O |
| HETATM | 799 | 1H | HOH | 21 | 13.745 | 10.082 | -9.473 | 1.00 | 0.00 | H |
| HETATM | 800 | 2H | HOH | 21 | 14.142 | 10.063 | -8.014 | 1.00 | 0.00 | H |
| HETATM | 801 | O | HOH | 22 | 11.244 | 11.155 | -10.623 | 1.00 | 56.60 | O |
| HETATM | 802 | 1H | HOH | 22 | 10.350 | 11.480 | -10.481 | 1.00 | 0.00 | H |
| HETATM | 803 | 2H | HOH | 22 | 11.708 | 11.979 | -10.633 | 1.00 | 0.00 | H |
| HETATM | 804 | O | HOH | 23 | 4.167 | 17.232 | 14.430 | 1.00 | 59.26 | O |
| HETATM | 805 | 1H | HOH | 23 | 3.234 | 17.266 | 14.255 | 1.00 | 0.00 | H |

FIG. 5N

| | | | | | | | | | |
|---|---|---|---|---|---|---|---|---|---|
| HETATM | 806 | 2H | HOH | 23 | 4.325 | 17.835 | 15.160 | 1.00 0.00 | H |
| HETATM | 807 | O | HOH | 24 | 7.289 | 13.019 | 7.362 | 1.00 59.36 | O |
| HETATM | 808 | 1H | HOH | 24 | 6.985 | 13.870 | 7.006 | 1.00 0.00 | H |
| HETATM | 809 | 2H | HOH | 24 | 6.571 | 12.413 | 7.174 | 1.00 0.00 | H |
| HETATM | 810 | O | HOH | 25 | 7.898 | 10.616 | 4.187 | 1.00 53.34 | O |
| HETATM | 811 | 1H | HOH | 25 | 8.656 | 10.430 | 4.750 | 1.00 0.00 | H |
| HETATM | 812 | 2H | HOH | 25 | 8.245 | 10.424 | 3.311 | 1.00 0.00 | H |
| HETATM | 813 | O | HOH | 26 | 18.700 | 5.086 | 6.487 | 1.00 58.77 | O |
| HETATM | 814 | 1H | HOH | 26 | 19.339 | 4.385 | 6.621 | 1.00 0.00 | H |
| HETATM | 815 | 2H | HOH | 26 | 18.262 | 5.154 | 7.320 | 1.00 0.00 | H |
| HETATM | 816 | O | HOH | 27 | 14.706 | 8.287 | -15.323 | 1.00 71.36 | O |
| HETATM | 817 | 1H | HOH | 27 | 13.983 | 8.106 | -15.937 | 1.00 0.00 | H |
| HETATM | 818 | 2H | HOH | 27 | 15.493 | 8.205 | -15.863 | 1.00 0.00 | H |
| HETATM | 819 | O | HOH | 28 | 17.583 | 10.761 | -18.187 | 1.00 49.62 | O |
| HETATM | 820 | 1H | HOH | 28 | 17.448 | 10.166 | -18.942 | 1.00 0.00 | H |
| HETATM | 821 | 2H | HOH | 28 | 17.684 | 10.091 | -17.473 | 1.00 0.00 | H |
| HETATM | 822 | O | HOH | 29 | 15.849 | 14.385 | -20.221 | 1.00 59.72 | O |
| HETATM | 823 | 1H | HOH | 29 | 16.623 | 13.960 | -19.443 | 1.00 0.00 | H |
| HETATM | 824 | 2H | HOH | 29 | 16.025 | 14.098 | -20.716 | 1.00 0.00 | H |
| HETATM | 825 | O | HOH | 30 | 23.359 | 25.370 | 14.837 | 1.00 57.74 | O |
| HETATM | 826 | 1H | HOH | 30 | 23.884 | 26.063 | 14.430 | 1.00 0.00 | H |
| HETATM | 827 | 2H | HOH | 30 | 23.387 | 25.608 | 15.758 | 1.00 0.00 | H |
| HETATM | 828 | O | HOH | 31 | 17.498 | 22.874 | 16.925 | 1.00 93.45 | O |
| HETATM | 829 | 1H | HOH | 31 | 17.242 | 23.753 | 16.701 | 1.00 0.00 | H |
| HETATM | 830 | 2H | HOH | 31 | 16.839 | 22.592 | 17.567 | 1.00 0.00 | H |
| HETATM | 831 | O | HOH | 32 | 20.348 | 23.693 | 23.117 | 1.00 63.40 | O |
| HETATM | 832 | 1H | HOH | 32 | 21.038 | 23.780 | 23.785 | 1.00 0.00 | H |
| HETATM | 833 | 2H | HOH | 32 | 20.407 | 22.764 | 22.840 | 1.00 0.00 | H |
| HETATM | 834 | O | HOH | 33 | 26.302 | 25.733 | 28.760 | 1.00 74.83 | O |
| HETATM | 835 | 1H | HOH | 33 | 26.307 | 26.586 | 28.361 | 1.00 0.00 | H |
| HETATM | 836 | 2H | HOH | 33 | 25.982 | 25.835 | 29.661 | 1.00 0.00 | H |
| HETATM | 837 | O | HOH | 34 | 25.950 | 24.779 | 25.047 | 1.00 73.62 | O |
| HETATM | 838 | 1H | HOH | 34 | 26.734 | 24.588 | 25.612 | 1.00 0.00 | H |
| HETATM | 839 | 2H | HOH | 34 | 26.332 | 25.366 | 24.401 | 1.00 0.00 | H |
| HETATM | 840 | O | HOH | 35 | 11.696 | 17.842 | 0.575 | 1.00 63.54 | O |
| HETATM | 841 | 1H | HOH | 35 | 12.559 | 17.505 | 0.750 | 1.00 0.00 | H |
| HETATM | 842 | 2H | HOH | 35 | 11.078 | 17.126 | 0.562 | 1.00 0.00 | H |
| HETATM | 843 | O | HOH | 36 | 14.262 | 19.203 | 4.844 | 1.00 48.44 | O |
| HETATM | 844 | 1H | HOH | 36 | 13.591 | 19.435 | 5.469 | 1.00 0.00 | H |
| HETATM | 845 | 2H | HOH | 36 | 15.124 | 19.290 | 5.226 | 1.00 0.00 | H |
| HETATM | 846 | O | HOH | 37 | 15.984 | 22.052 | -2.490 | 1.00 62.80 | O |
| HETATM | 847 | 1H | HOH | 37 | 15.327 | 21.946 | -3.200 | 1.00 0.00 | H |
| HETATM | 848 | 2H | HOH | 37 | 15.529 | 21.751 | -1.706 | 1.00 0.00 | H |
| HETATM | 849 | O | HOH | 38 | 16.135 | 20.908 | -5.213 | 1.00 82.35 | O |
| HETATM | 850 | 1H | HOH | 38 | 16.482 | 20.062 | -4.835 | 1.00 0.00 | H |
| HETATM | 851 | 2H | HOH | 38 | 15.378 | 20.538 | -5.665 | 1.00 0.00 | H |
| HETATM | 852 | O | HOH | 39 | 10.937 | 6.573 | -6.161 | 1.00 63.06 | O |
| HETATM | 853 | 1H | HOH | 39 | 11.244 | 5.996 | -5.478 | 1.00 0.00 | H |
| HETATM | 854 | 2H | HOH | 39 | 11.691 | 7.003 | -6.564 | 1.00 0.00 | H |
| HETATM | 855 | O | HOH | 40 | 9.077 | 12.911 | -2.911 | 1.00 64.88 | O |
| HETATM | 856 | 1H | HOH | 40 | 8.184 | 13.199 | -3.064 | 1.00 0.00 | H |
| HETATM | 857 | 2H | HOH | 40 | 9.394 | 12.597 | -3.765 | 1.00 0.00 | H |
| HETATM | 858 | O | HOH | 41 | 13.272 | 7.391 | 13.889 | 1.00 65.83 | O |
| HETATM | 859 | 1H | HOH | 41 | 13.756 | 6.842 | 13.286 | 1.00 0.00 | H |
| HETATM | 860 | 2H | HOH | 41 | 13.421 | 8.306 | 13.606 | 1.00 0.00 | H |
| HETATM | 861 | O | HOH | 42 | 6.871 | 10.837 | 16.390 | 1.00 58.39 | O |
| HETATM | 862 | 1H | HOH | 42 | 6.258 | 11.055 | 15.679 | 1.00 0.00 | H |
| HETATM | 863 | 2H | HOH | 42 | 7.611 | 11.410 | 16.223 | 1.00 0.00 | H |

FIG. 50

```
HETATM  864  O   HOH  43    14.184  12.148  23.463  1.00  73.66        O
HETATM  865 1H   HOH  43    14.543  11.552  22.797  1.00   0.00        H
HETATM  866 2H   HOH  43    13.316  12.368  23.168  1.00   0.00        H
END
```

FIG. 5P

SEQUENCE LISTING

<160> NUMBER OF SEQ ID NOS: 2

<210> SEQ ID NO 1
<211> LENGTH: 36
<212> TYPE: PRT
<213> ORGANISM: Human Immunodeficiency Virus

<400> SEQUENCE: 1

Ser Gly Ile Val Gln Gln Gln Asn Asn Leu Leu Arg Ala Ile Glu Ala
 1               5                  10                  15

Gln Gln His Leu Leu Gln Leu Thr Val Trp Gly Ile Lys Gln Leu Gln
            20                  25                  30

Ala Arg Ile Leu
        35

<210> SEQ ID NO 2
<211> LENGTH: 34
<212> TYPE: PRT
<213> ORGANISM: Human Immunodeficiency Virus

<400> SEQUENCE: 2

Trp Met Glu Trp Asp Arg Glu Ile Asn Asn Tyr Thr Ser Leu Ile His
 1               5                  10                  15

Ser Leu Ile Glu Glu Ser Gln Asn Gln Gln Glu Lys Asn Glu Gln Glu
            20                  25                  30

Leu Leu

CORE STRUCTURE OF GP41 FROM THE HIV ENVELOPE GLYCOPROTEIN

RELATED APPLICATION(S)

This application is a continuation of U.S. application Ser. No. 10/200,007, now abandoned, entitled, "Core Structure of gp41 from the HIV Envelope Glycoprotein," by David C. Chan, Deborah Fass, Min Lu, James M. Berger and Peter S. Kim, filed Jul. 18, 2002, which is a continuation of U.S. application Ser. No. 09/484,925, now U.S. Pat. No. 6,506,554, entitled "Core Structure of gp41 From the HIV Envelope Glycoprotein", by David C. Chan, Deborah Fass, Min Lu, James M. Berger and Peter S. Kim, filed Jan. 18, 2000, which is a Divisional Application of No. 09/062,241, entitled, "Core Structure of gp41 From the HIV Envelope Glycoprotein", by David C. Chan, Deborah Fass, Min Lu, James M. Berger and Peter S. Kim, (filed on Apr. 17, 1998) now U.S. Pat. No. 6,150,088 (issued Nov. 21, 2000), which claims the benefit of U.S. Provisional Application No. 60/043,280, entitled "Core Structure of gp41 from the HIV Envelope Glycoprotein", by David C. Chan, Deborah Fass, Min Lu, James M. Berger and Peter S. Kim (filed Apr. 17, 1997). The entire teachings of the above applications are incorporated herein by reference.

GOVERNMENT SUPPORT

Work described herein was funded by the Howard Hughes Medical Institute.

BACKGROUND OF THE INVENTION

The surface glycoproteins of enveloped viruses play critical roles in the initial events of viral infection, mediating virion attachment to cells and fusion of the viral and immune response in infected hosts. Envelope glycoproteins are also major targets for the anti-viral immune response in infected hosts. The human immunodeficiency virus type 1 (HIV-1) envelope glycoprotein consists of two noncovalently associated subunits, gp120 and gp41, that are generated by proteolytic cleavage of a precursor polypeptide, gp160. Luciw, P. A., *In Fields Virology*, Third Edition, B. N. Fields et al., eds., Lippincott-Raven Publishers, Philadelphia, pp. 1881-1952 (1996); Freed, E. O. et al., *J. Biol. Chem.* 270: 23883-23886 (1995). gp120 directs target-cell recognition and viral tropism through interaction with the cell-surface receptor CD4 and one of several co-receptors that are members of the chemokine receptor family. Broder, C. C. et al., *Pathobiology* 64:171-179 (1996); D'Souza, M. P. et al., *Nature Med.* 2:1293-1300 (1996); Wilkinson, D., *Current Biology* 6:1051-1053 (1996). The membrane-spanning gp41 subunit then promotes fusion of the viral and cellular membranes, a process that results in the release of viral contents into the host cell. It has not yet been possible to obtain a detailed structure for gp41, either alone or in complex with gp120.

SUMMARY OF THE INVENTION

Described herein is the crystal structure of the α-helical domain of the gp41 component of HIV-1 envelope glycoprotein which represents the core of fusion-active gp41. Also described herein is Applicants' determination, with reference to the crystal structure, that certain amino acid residues within the core are essential for interaction of the component peptides and, thus, for gp41 activity. The core of fusion-active gp41 is composed of a trimer of two interacting peptides, referred to here as N36 and C34. The minimal stable envelope subdomain has been shown to consist of a 36-residue peptide (N-36) and a 34-residue peptide (C-34) whose amino acid sequences are presented below. The crystal structure of the N36/C34 complex is a six-helix bundle in which three N36 helices form an interior, parallel coiled coil and three C34 helices pack in an oblique, anti-parallel manner into highly conserved, hydrophobic grooves on the surface of the N36 trimer. It shows striking similarity to the low-pH induced conformation of influenza hemagglutinin (HA).

Applicants have determined the structural basis for interaction between two peptide fragments of HIV gp41: one peptide fragment derived from the N-terminal region of the ectodomain of gp41 and one peptide fragment derived from the C-terminal region of the gp41 ectodomain. The N-terminal peptide fragment, N36, includes amino acid residue 546 through and including amino acid residue 581, numbered according to their position in HIV-1 gp160; it includes amino acid residues which comprise a region of the ectodomain which encompasses the 4-3 hydrophobic repeat. The amino acid sequence of the N36 peptide is:

SGIVQQQNNLLRAIEAQQHLLQLTVWGIKQLQRIL (SEQ ID NO.: 1). The C-terminal region peptide fragment C34 includes amino acid residue 628 through and including amino acid residue 661, numbered according to their position in HIV-1 gp160; it is derived from the region prior to the transmembrane segment. The amino acid sequence of the C34 peptide is:

WMEWDREINNYTSLIHSLIEESQNQQEKNEQELL (SEQ ID NO.: 2). The three-dimension coordinates for the atoms in the N36/C34 gp41 complex are presented herein. They can be used to display the structure of the complex and to design molecules (drugs) which interact with gp41 and inhibit its activity, such as those which prevent interaction of key components (amino acid residues) of the α-helical domain which represents the core of fusion-active gp41.

Work described herein provides, for the first time, an understanding of how the N-terminal peptide and the C-terminal peptide interact. The crystal structure and information regarding the interactions of these two peptides provide the basis for development of drugs which inhibit HIV infection, such as peptidomimetic or small-molecule inhibitors, using such methods as combinatorial chemistry or rational drug design. Drugs developed or identified with reference to the information provided herein are also the subject of the present invention. Drugs which fit into or line the N-peptide cavity, prevent the N-peptide cavity from accommodating amino acid residues or peptides from the C-terminal region of gp41 and, thus, prevent or inhibit gp41 activity are the subject of this invention. Such drugs can be identified with reference to the information about the structure of the complex and the cavity shown to be present in the N36 trimer, provided herein, or with reference to information about the structure of the complex and the three dimensional coordinates of the cavity, also provided herein, and known methods. In a particular embodiment of identifying or designing a molecule which inhibits the fusion active form of gp41 and, thus, inhibit HIV, in which combinatorial chemistry is used, a library biased to include an increased number of indole rings, hydrophobic moieties and/or negatively charged molecules is used. An antibody which binds these key areas of fusion-active gp41 is also the subject of the invention. For example, an immunogen which is or includes a molecule with the coordinates described herein or the N-peptide core can be used to immunize an individual, resulting in production of antibodies that bind the cavity or pocket on the N-terminal peptide and, thus, render it unavailable for its normal interactions and prevent or inhibit gp41 activity.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 3A shows an end-on view of the N36/C34 complex looking down the three-fold axis of the trimer. FIG. 3B shows a side view with one N36 and one C34 helix labeled. The amino termini of the N36 helices (grey) point towards the top of the page, while those of the C34 helices (black) point towards the bottom. Diagrams were prepared using the program MOLSCRIPT (Kraulis, P., *J. Appl. Cryst.* 24:924-950 (1991)).

FIGS. 5A-5P present the three-dimension coordinates for the atoms in the N36/C34 gp41 complex; the atom types (column 3) in each amino acid (column 4) are listed, along with their coordinates (columns 6, 7, 8) in space. The three-dimension coordinates can be used to display the structure of the N36/C34 complex. The coordinates are available from the Protein Data Bank at the Brookhaven National Laboratory.

DETAILED DESCRIPTION OF THE INVENTION

Figure 1:
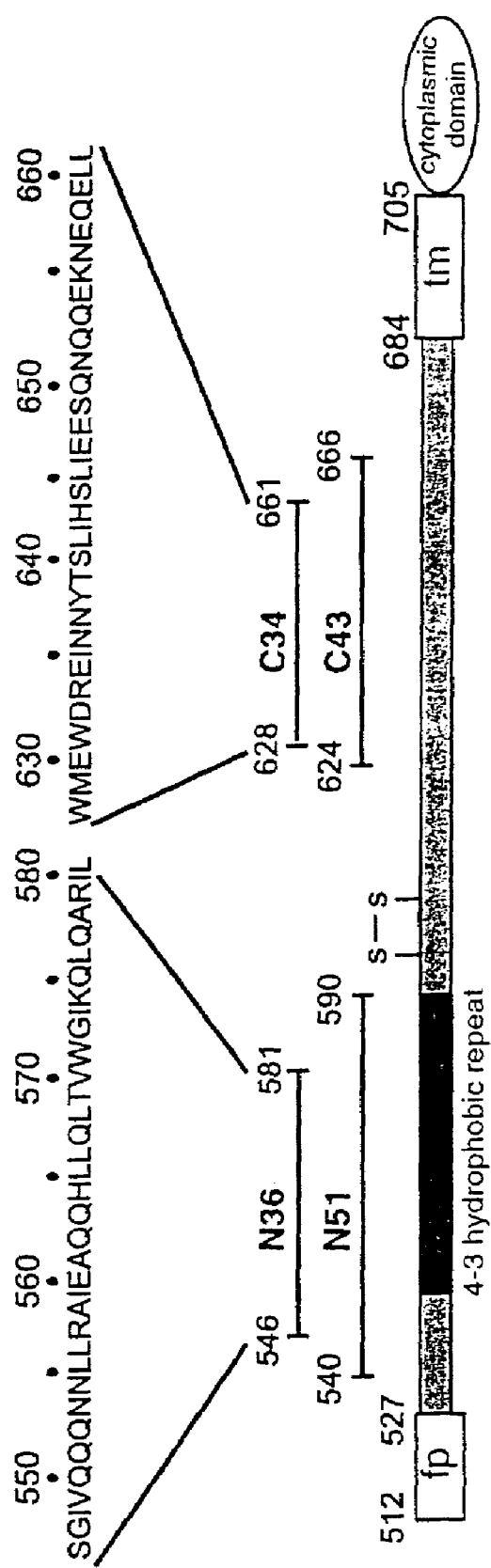
FIG. 1 is a schematic view of gp41 showing important functional regions, including the 4-3 hydrophobic repeat, the fusion peptide (fp), a disulfide linkage (S—S), and the transmembrane region (tm). The ectodomain is drawn approximately to scale. The peptides identified by protein dissection are shown above, along with the sequences of N36 and C34. The residues are numbered according to their position in gp160.

For the first time, a high-resolution picture of the protein fragment that enables HIV to invade human cells has been produced. As described, Applicants have determined the crystal structure of a key fragment of the HIV envelope protein. The envelope protein resides on the surface of the virus and plays a crucial role in HIV infection. One part of the protein, known as gp120, allows the virus to bind to human cells. Another subunit, gp41, mediates fusion of the viral membrane and the cell membrane—it initiates entry of the virus into the cell. The core structure of gp41 has been determined using X-ray crystallography.

The images of the protein fragment reveal a compact, six-helix bundle punctuated by deep cavities which are key targets for the development of new antiviral drugs. The existence of the cavities could not have been determined without the images.

Despite its importance, there are no antiviral drugs that target the envelope protein of HIV, in part because the virus is extraordinarily clever at changing the pieces of the protein it presents to the outside world. Work presented herein shows that the cavity structure may not be so amenable to change; therefore, drugs directed towards this region are useful against many HIV strains.

The HIV fusion protein has characteristics similar to those of the fusion structure of influenza virus. Surprisingly, the HIV fusion protein has a deep cavity or pocket at the base of each groove in the N36 coiled coil. In the active structure, each cavity is filled by a knob-like protrusion from C34. This ball-and-socket arrangement of C34 and N36 is a target for drug design or discovery. The structure, combined with data from other laboratories, supports the idea that a small molecule constructed specifically to block this interaction will stop fusion and prevent the virus from entering cells.

There are at least three reasons why such a molecule would be effective in preventing HIV from entering cells. First, test tube studies have shown that fragments, or peptides, of gp41 encompassing or overlapping with N36 or C34 have potent anti-viral activity. However, peptides generally make poor drugs because they are poorly absorbed and the body breaks them down almost immediately. A small molecule targeting just the cavity structure could escape this fate.

Second, the inhibitors derived from the C and N peptides are effective in the test tube against a wide range of HIV strains, including patient isolates and laboratory-adapted strains. By contrast, neutralizing antibodies and drug candidates designed to block the binding activity of the envelope protein are typically effective against only a limited subset of HIV strains.

Third, alteration of the walls of the N36 cavity can block the fusion reaction, indicating that the ball-and-socket arrangement of N36 and C34 must be preserved to obtain viral infection. In addition, the protein building blocks that make up the walls are highly conserved among HIV strains and between HIV and SIV, the virus responsible for AIDS in monkeys. This suggests that the virus cannot tolerate much change in this region and that HIV may have more difficulty developing resistance to a cavity-blocking drug than to many other compounds.

Applicants have analyzed the crystal structure of the α-helical domain of the HIV-1 transmembrane protein gp41 by means of assessment of a complex, referred to herein as the N36/C34 complex, which is composed of two interacting peptides: N36, which is derived from the N-terminal region of the gp41 ectodomain and C34, which is derived from the C-terminal region of the gp41 ectodomain. As described herein, Applicants have shown that the N36/C34 complex is a six-helix bundle (FIG. 3), in which the center consists of a parallel, trimeric coiled-coil of three N36 helices wrapped in a gradual left-handed superhelix. Three C34 helices wrap antiparallel to the N36 helices in a left-handed direction around the outside of the central coiled-coil N36 trimer. The N36/C34 complex is a cylinder which is approximately 35 Å in diameter and approximately 55 Å in height. FIG. 4 is a helical wheel representations of N36 and C34 in which three N36 helices and one C34 helix are represented as helical wheel projections. As can be seen, the interior amino acid residues at the a and d positions of the N36 heptad repeat are predominately hydrophobic (isoleucine, leucine). The characteristic "knobs-into-holes" packing of coiled coils occurs in the N36 trimer. That is, the amino acid residues (knobs) at the a and d layers pack into cavities (holes) between four residues of an adjacent helix. Crick, F. H. C., *Acta. Cryst.,* 6: 689-697 (1953); O'Shea, E. K., et al., *Science,* 254:539-544 (1991). Further description of the N36 trimer is presented in Example 2.

An electrostatic potential map of the cylindrical N36 superhelix shows that the surface of the superhelix is largely uncharged. The grooves that are the sites for C34 interaction have been determined to be lined with predominantly hydrophobic amino acid residues. The surface of the N36/C34 complex is much more highly charged than the isolated N-peptides, due to the acidic residues on the outside of the C34 helices. This explains why the heterodimeric complex exhibits greater solubility than the isolated peptides.

Three C34 helices pack obliquely against the outside of the N36 coiled-coil trimer in an antiparallel orientation. Interaction between the C34 helices and N36 occurs mainly through hydrophobic residues in three grooves on the surface of the central coiled-coil trimer. The amino acid residues which line these grooves are highly conserved between HIV and SIV gp41. In contrast, the N36 residues which flank the C34 helices are divergent. The pattern of sequence conservation is also apparent on the helical wheel representation of three N36 helices and one C34 helix of FIG. 4. (See Example 3.)

Each of the grooves on the surface of the N36 trimer has a particularly deep cavity. The cavity is approximately 16 Å long, approximately 7 Å wide and approximately 5-6 Å deep. It accommodates three hydrophobic amino acid residues from the abutting C34 helix: isoleucine-635 ($I_{635}$), tryptophan-631 ($W_{631}$) and tryptophan-628 ($W_{628}$). The top of the N36 cavity is lined by leucine-566 (Leu-566) of the left N36 helix and leucine-565 (Leu-565) of the right N36 helix. The left side of the cavity is formed by side chains from the left N36 helix, including amino acid residues (top to bottom): valine-570 (Val-570), lysine-574 (Lys-574, aliphatic portion) and glutamine-577 (Gln-577). The right wall of the cavity is formed by amino acid residues leucine-568 (Leu-568), tryptophan-571 (Trp-571) and glycine-572 (Gly-572) of the right N36 helix. The cavity floor is composed of threonine-569 (Thr-569), isoleucine-573 (Ile-573) and leucine-576 (Leu-576). Thus, interactions within the cavity are predominantly hydrophobic. In addition, aspartic acid-632 (Asp-632) of C34 forms a conserved salt bridge with lysine-574 (Lys-574) of N36 immediately to the left of the cavity.

As a result of the work described, a region of the HIV-1 transmembrane protein gp41 which is a target for HIV inhibitors has been defined and is available for designing and/or developing new drugs and identifying existing drugs which inhibit HIV. A particularly valuable target for an HIV inhibitor are the highly conserved, deep cavities on the N-peptide coiled-coil trimer that accommodate C-peptide amino acid residues. The amino acid residues which form the cavity have been defined. Thus, a drug (e.g., a peptide, peptidomimetic, small molecule or other agent) which fits into or lines the N-peptide cavity or socket, prevents the N-peptide cavity from accommodating peptides from the C-terminal region of gp41 and, thus, prevents or inhibits gp41 activity, can be identified or designed. For example, a drug which fits into or lines the cavity can be identified or designed, using known methods. One such drug is a molecule or compound which fits into or lines a cavity:

a) lined by Leu-566 of the left N36 helix and Leu-565 of the right N36 helix;
b) formed on the left side by sidechains from the left N36 helix, including residues (top to bottom) Val-570, Lys-574 (aliphatic portion) and Gln-577;
c) formed on the right side by residues Leu-568, Trp-571 and Gly-572 of the right N36 helix; and
d) composed on its floor of Thr-569, Ile-573 and Leu-576.

Figure 6:
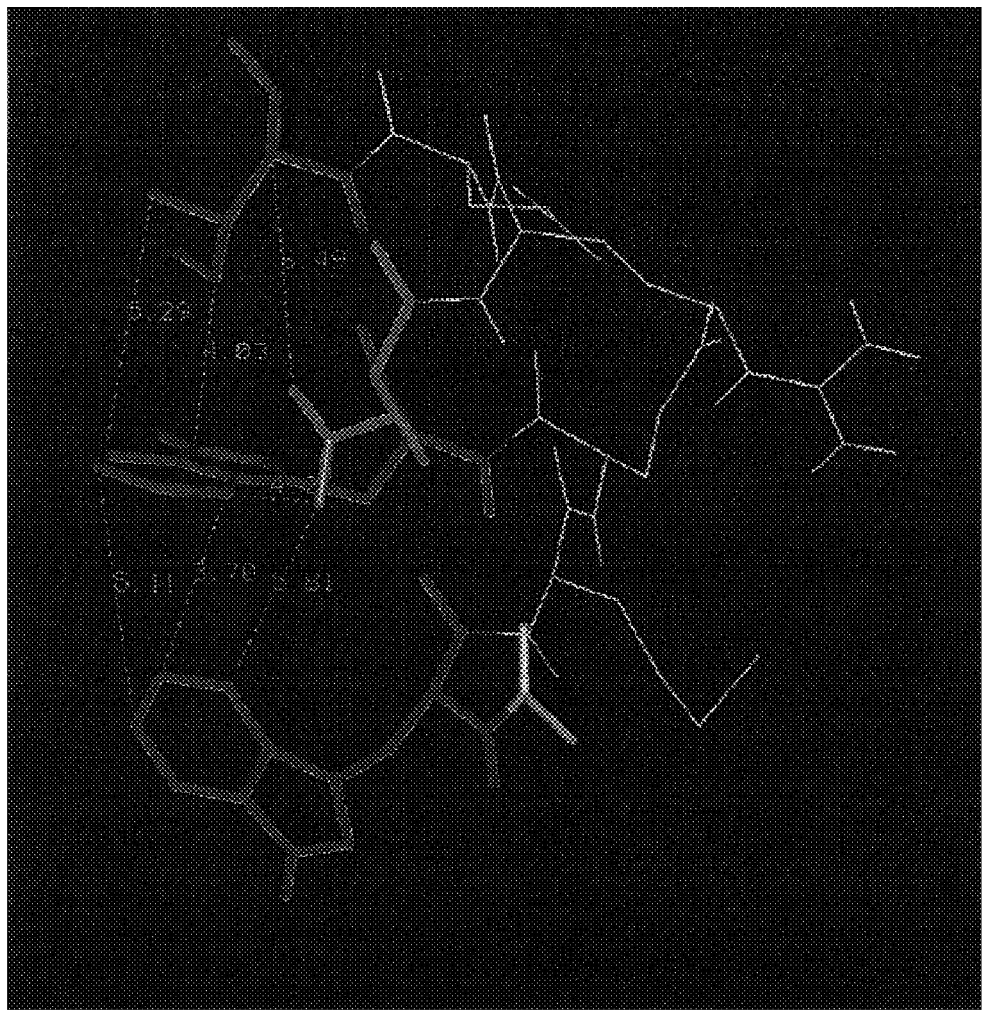
FIG. 6 represents the distances (in Å) between the atoms in the four amino acid residues of C34 that dock into the cavity on the N36 trimer surface. The two tryptophan residues, and the isoleucine residue and the aspartic acid residue are indicated in green.

The cavities present on the N-peptide coiled-coil trimer each accommodate three hydrophobic amino acid residues from the abutting C34 helix: Ile-635, Trp-631 and Trp-628 and a negatively charged amino acid residue from C34: Asp-632, which forms a conserved salt bridge with Lys-574 of N36 immediately to the left of the cavity. A drug which mimics the ability of these three residues (Trp-Trp-Ile) to fit into or line N36 cavities can also be developed. Such a drug can be developed, for example, with reference to the three-dimension coordinates provided (FIGS. 5A-5P) and the information provided (FIG. 6, for example) regarding the distances between the atoms in the four amino acid residues of C34 that dock into the cavity on the N36 trimer surface.

For example, a structure-based approach can be used, along with available computer-based design programs, to identify or design a drug which will fit into, line or bind a cavity or pocket on N36 (or block C34 from doing so) and inhibit or prevent the activity of gp41 and, as a result, reduce (partially or totally) the ability of HIV-1 to infect cells. In one embodiment of the present invention, the following method is carried out to design or identify a molecule or drug which inhibits gp41 activity (and reduces HIV-1 infection of cells) by fitting into or lining the N36 cavity. In a computer processor having a digital processor, a method of designing or identifying a drug or molecule which inhibits (totally or partially) the interaction of N36 and C34 or fits into or lines a cavity on N36, comprises the steps of: (a) providing a library of molecules, compounds or drugs whose crystal structures, coordinates, chemical configurations or structures are known; (b) providing a crystal structure of a target molecule, which is the α-helical domain of the gp41 component of HIV-1 envelope glycoprotein which represents the core of fusion-active gp41 (referred to for convenience as the N36/C34 complex or N36/C34); and (c) comparing coordinates, crystal structure components, chemical configurations or structures of members of the library of molecules with those of the target molecule, such as by using a processor routine executed by the digital processor to search the library to find a molecule or a molecule component which fits into or lines the cavity on N36, the processor routine providing design or identification of a member or members of the library which fit into or line the cavity on N36 or a member or members which comprise a component moiety or component moieties which fit into or line the cavity on N36. For example, this method can be carried out by comparing the members of the library with the crystal structure of gp41 N36/C34 presented herein using computer programs known to those of skill in the art (e.g., Dock, Kuntz, I. D. et al., *Science,* 257:1078-1082 (1992); Kuntz, I. D. et al., *J. Mol. Biol.,* 161:269 (1982); Meng, E. C., et al., *J. Comp.Chem.,* 13:505-524 (1992) or CAVEAT).

In the method, the library of molecules to be searched in (a) can be any library, such as a database (i.e., online, offline, internal, external) which comprises crystal structures, coordinates, chemical configurations or structures of molecules, compounds or drugs (referred to collectively as to be assessed or screened for their ability inhibit N36/C34 interaction candidate N36 ligands). For example, databases for drug design, such as the Cambridge Structural Database (CSD), which includes about 100,000 molecules whose crystal structures have been determined or the Fine Chemical Director (FCD) distributed by Molecular Design Limited (San Leandro, Calif.) can be used. [CSD: Allen, F. H., et al., *Acta Crystallogr. Section B,* 35:2331 (1979)] In addition, a library, such as a database, biased to include an increased number of members which comprise indole rings, hydrophobic moieties and/or negatively-charged molecules can be used.

Coordinates of the molecules in the library can be compared in the method to coordinates of the cavity on N36 or to coordinates of C36 and its components which fit into or line an N36 cavity or pocket. The cavity on N36 is described in detail herein, as are key components of C34 which are accommodated by cavities on the N-peptide. Upon finding a match to coordinates of at least one molecule in the library, at least one member is, thus, determined or identified as an N36 ligand (at least one member is determined to be a member which will inhibit N36/C34 interaction).

Additional steps in the searching process can include combining certain library members or components of library members to form collective coordinates or molecules which combine features or coordinates of two or more library members; comparing the resulting collective coordinates or molecules with the crystal structure of the target molecule and identifying those which will interact with an N36 cavity (or cavities).

Upon identification of an existing drug or design of a novel molecule as described herein, its ability to line or fit into a cavity on N36 or block N36/C34 interaction can be assessed using known methods, such as by expressing N36 and C34 in an appropriate host cell (e.g., a bacterial cell containing and expressing DNA encoding N36 and C34), combining the expressed products with the drug to be assessed and determining whether it interferes with the interaction of N36 and C34, lines a cavity on N36 and C34. Drugs which are found to do so can be assessed in additional assays, both in vitro and in vivo (e.g., an appropriate animal model challenged by HIV infection). Once a drug has been identified or designed, it may be desirable to refine or reconfigure it in such a manner that a drug which binds better (e.g., with greater specificity and/or affinity) is produced. In this case, the processor routine further determines the quality of matches and calculates a goodness of fit, making it possible to do so.

A drug or molecule which binds or fits into a cavity or pocket on the surface of N36, can be used alone or in combination with other drugs (as part of a drug cocktail) to prevent or reduce HIV infection of humans. A drug designed or formed by a method described herein is also the subject of this invention.

Also the subject of this invention is a method of treating an individual infected with HIV or at risk of being infected with HIV, in order to reduce the extent of infection or to prevent infection. In the method, a drug which fits into, lines or binds a cavity or cavities on N36 is administered to the individual, alone or in combination with other drugs.

A further subject of this invention is an immunogen based on a molecule with coordinates as described herein which is used to produce antibodies that bind the N36 cavity or pocket and, thus, prevent N36/C34 interaction and inhibit gp41 activity. For example, the N-peptide core can be used, in known methods, to produce polyclonal or monoclonal antibodies, which can be administered to an individual. Alternatively, an individual (e.g., a human infected with HIV or at risk or being infected) can be immunized with the N-peptide core. The individual will, as a result, produce antibodies which will bind the N36 pocket or cavity and prevent or reduce gp41 activity. Thus, this invention also relates to a vaccine to reduce or prevent gp41 function (and, as a result, HIV infection).

As described above, Applicants have provided the identity of amino acid residues which form the cavity into which amino acid residues of the gp41 C-peptides fit. Thus, they have defined target amino acid residues which can be mutated or modified, individually or jointly, to further assess the structural basis for interaction between the two peptides, identify amino acid residues essential for the two to fit together and design or identify molecules or compounds which inhibit/prevent the two helices from fitting together and, thus, inhibit or prevent gp41 membrane—fusion activity.

Numerous studies have led to the proposal that there are native (nonfusogenic) and fusion-active (fusogenic) states of viral membrane fusion proteins. Extensive conformational changes in the HIV envelope complex are thought to be involved in the transition from the native to the fusogenic state. Binding of CD4 to gp120 exposes the V3 loop of gp120, which likely interacts with the co-receptors. Choe, H. et al., *Cell* 85:1135-1148 (1996); Trkola, A. et al., *Nature* 384:184-187 (1996); Wu, L. et al., *Nature* 384:179-183 (1996). For some laboratory-adapted isolates of HIV-1, the conformational changes in gp120 upon CD4 binding are sufficient to cause gp120 to physically dissociate or "shed" from the viral surface, leaving the membrane-anchored gp41 subunit behind. Hart, T. K. et al., *Proc. Natl. Acad. Sci., USA* 88:2189-2193 (1991); Moore, J. P. et al., *Science* 250:1139-1142 (1990). Primary isolates of the virus generally do not shed gp120 readily in the presence of CD4 alone, although CD4 binding still induces conformational changes in gp120. (Sattentau, Q. J. et al., *Phil. Trans. Royal Soc. B* 342:59-66 (1993); Sattentau, Q. J. et al., *J. Virol.* 67:7383-7393 (1993); Sullivan, N. et al., *J. Virol.* 69:4413-4422 (1995), Stamatatos, L. et al., *J. Virol.* 69:6191-6198 (1995)).

CD4 binding also induces conformational changes in gp41, as inferred from changes in antibody binding and sensitivity to limited proteolysis (Sattentau, Q. J. et al., *Phil. Trans. Royal Soc. B* 342:59-66 (1993); Sattentau, Q. J. et al., *J. Virol.* 67:7383-7393 (1993)). Moreover, addition of low levels of soluble CD4 enhances the infectivity of some viral isolates, suggesting that the gp 120/gp41 conformational changes induced by CD4 play a role in membrane fusion (Allan, J. S. et al., *Science* 247:1084-1088 (1990); Sullivan, N. et al., *J. Virol.* 69:4413-4422 (1995)). These conformational changes are thought to expose the hydrophobic, glycine-rich fusion-peptide region of gp41 that is essential for membrane-fusion activity.

To obtain a detailed structure for gp41, a protein-dissection approach, in which key substructures of a protein are identified and studied was applied. See, for example, Oas, T. G. et al., *Nature* 336:42-48 (1988). Limited proteolysis of a fragment corresponding to the ectodomain of gp41 generated a stable, soluble complex composed of two peptide fragments denoted N51 and C43 (FIG. 1) that are derived from the N- and C-terminal regions of the ectodomain, respectively (Lu, M. et al., *Nature Struct. Biol.* 2:1075-1082 (1995)). In gp41, the region following the fusion peptide has a high α-helical propensity and a 4-3 heptad repeat of hydrophobic residues, a sequence feature characteristic of coiled coils. Chambers, P. et al., *J. Gen. Virol.* 71:3075-3080 (1990); Delwart, E. L. et al., *AIDS Res. Hum. Retroviruses* 6:703-706 (1990); Gallaher, W. R. et al., *AIDS Res. Hum. Retroviruses* 5:431-440 (1989). The N51 peptide corresponds to the 4-3 hydrophobic repeat region adjacent to the fusion peptide, while the C43 peptide is derived from the region prior to the transmembrane segment (FIG. 1).

Interestingly, isolated peptides that overlap, or are derived from, the N51 and C43 regions of gp41 can have potent anti-viral activity (Wild, C. T. et al., *Proc. Natl. Acad. Sci., USA* 89:10537-10541 (1992); Wild, C. T. et al., *Proc. Natl. Acad. Sci., USA* 91:9770-9774 (1994); Jiang, S. et al., *Nature* 365:113 (1993)). Peptides from the C-terminal region of the ectodomain have the highest activity. Consistent with these studies, both N51 and C43 are capable of inhibiting HIV envelope-mediated cell fusion; the C43 peptide exhibits 10-fold greater activity than N51 (Lu, M. et al., *Nature Struct. Biol.* 2:1075-1082 (1995)). The inhibitory activity of the C43 peptide, however, is markedly reduced when stoichiometric amounts of N51 are present, suggesting that the C43 peptide inhibits membrane fusion in a dominant-negative manner, by associating with an N51 region within intact gp41 (Lu, M. et al., *Nature Struct. Biol.* 2:1075-1082 (1995)). Thus, in addition to providing insights into the mechanism of membrane fusion, determining the structural basis for interaction between the N51 and C43 regions will assist anti-viral drug-development efforts.

Biophysical studies showed that the N51 and C43 peptides associate to form a highly thermostable, helical, trimeric complex of heterodimers, in which the N51 and C43 helices are oriented in an antiparallel manner. Lu, M. et al., *Nature Struct. Biol.* 2:1075-1082 (1995). Analogous experiments with the gp41 ectodomain from simian immunodeficiency virus (SIV) gave almost identical results, indicating that the gp41 core identified in these protein-dissection studies is conserved among lentiviruses. Blacklow, S. C. et al., *Biochemistry* 34:14955-14962 (1995). On the basis of these results and other considerations, we proposed that the gp41 core consists of an interior coiled-coil trimer formed by the N51 region, against which three C43 helices pack. Lu, M. et al., *Nature Struct. Biol.* 2:1075-1082 (1995); Blacklow, S. C. et al., *Biochemistry* 34:14955-14962 (1995).

The thermal denaturation of the N51/C43 complexes from HIV-1 or SIV gp41 is irreversible, probably as a result of aggregation of the unfolded peptides at high temperature. Lu, M. et al., *Nature Struct. Biol.* 2:1075-1082 (1995); Blacklow, S. C. et al., *Biochemistry* 34:14955-14962 (1995). With a view towards crystallographic studies, further protein dissection experiments were used to define a smaller subdomain with more favorable thermodynamic properties. These studies led to the identification of the peptides N36 and C34 (FIG. 1). Like the longer peptides, N36 and C34 form a stable, trimeric complex of heterodimers with 100% α-helix content. Unlike the larger complex, however, the N36/C34 complex has a reversible thermal unfolding transition. Presented herein is the crystal structure of the N36/C34 complex solved to 2.0 Å resolution, as well as a discussion of the implications of this structure for HIV viral membrane fusion and its inhibition.

The work described herein provides good evidence that the structure of gp41 obtained is found in the fusion-active state of HIV envelope. That this is the core of gp41 in the fusogenic state is supported by several considerations.

First, the N36/C34 complex folds in the absence of gp120. The fusogenic state of gp41 is expected to be stable in the absence of gp120, since dissociation of gp120 from the envelope glycoprotein is thought to accompany the conversion from a native to a fusogenic state. Cohen, J., *Science* 274:502 (1996); Wilkinson, D., *Current Biology* 6:1051-1053, (1996). Similarly, the conversion of influenza HA2 to the fusogenic state is accompanied by loss of most of its contacts with HA1. Proteolysis of the low-pH converted form of HA prior to crystallization removes most of the receptor-binding HA1 subunit. Bullough, P. A. et al., *Nature* 371:37-43 (1994). Moreover, the structural features of the fusogenic state are preserved in fragments of HA2 that fold cooperatively in the complete absence of the HA1 subunit. Carr, C. M. et al., *Cell* 73:823-832 (1993); Chen, J. et al., *Proc. Natl. Acad. Sci., USA* 92:12205-12209 (1995).

Second, the isolated gp41 core is exceedingly stable to thermal denaturation. The N51/C43 complex has an apparent melting temperature of approximately 90° C. Lu, M. et al., *Nature Struct. Biol.* 2:1075-1082 (1995). In contrast, the native state of the HIV envelope glycoprotein is not particularly stable, as evidenced by the ease with which gp120 is shed in preparations of virus particles. Helseth, E. et al., *J. Virol.* 65:2119-2123 (1991); Kalyanaraman, V. S. et al., *AIDS Res. Hum. Retroviruses* 6, 371-380 (1990).

Third, mutations in gp41 that abolish infectivity and membrane fusion often map to residues that are expected to stabilize the gp41 core structure determined here. Numerous studies show that mutations in the 4-3 hydrophobic repeat region abolish membrane fusion, although these mutants tend to have additional defects. Dubay, J. W. et al., *J. Virol.* 66:4748-4756 (1992); Chen, S. S., *J. Virol.* 68:2002-2010 (1994); Chen, S. S. et al., *J. Virol.* 67, 3615-3619 (1993); Wild, C. et al., *Proc. Natl. Acad. Sci., USA* 91:12676-12680 (1994); Poumbourios, P., *J. Virol.* 71:2041-2049 (1997). The Leu-568→Ala, Trp-571→Arg, and Asn-656→Leu mutations are particularly noteworthy because cells expressing mutant envelope glycoproteins with one of these point mutations are completely defective in membrane fusion, as judged by an inability to form syncytia with CD4-positive human lymphocyte lines, even though the mutant proteins exhibit substantial cell-surface expression, CD4 binding, gp120/gp41 association, gp160 precursor processing, and soluble CD4-induced shedding. Cao, J. et al., *J. Virol.* 67:2747-2755 (1993). Leu-568 and Trp-571 are N36 residues that line the right wall of the cavity. Asn-656 is in an a position of the C34 peptide and packs against the central N36 coiled-coil trimer. The locations of these key mutations suggest that interactions between the N36 and C34 helices are critical for membrane fusion.

Fourth, that the N36/C34 structure corresponds to the core of the fusogenic state of gp41 is consistent with a large body of data on the inhibition of HIV-1 infection and syncytia formation by derivatives of the peptides that make up this core. This issue is discussed in more detail below. Finally, the structural similarity of the N36/C34 complex to the low-pH induced conformation of influenza HA2 (Bullough, P. A. et al., *Nature* 371:37-43 (1994)) and to the structure of Mo-MLV TM (Fass, D. et al., *Nature Struct. Biol.* 3:465-469 (1996)), each of which has been proposed to represent fusion-active conformations, supports the idea that N36/C34 is the core of the fusogenic conformation of gp41. For all three structures, the hydrophobic fusion peptide would be immediately amino terminal to a central, three-stranded coiled coil. In influenza HA2 and HIV-1 gp41, the central three-stranded coiled coils are each stabilized by three helices that pack obliquely against the coiled-coil trimer in an antiparallel manner. In the TM subunit of Mo-MLV, these obliquely packed helices are replaced by a short helix and an extended region that serve a similar structural role.

Work described herein also relates to inhibitors of HIV-1 infection and targets for developing new peptidomimetic or small-molecule inhibitors of HIV infection. Synthetic peptides containing approximately 40 residues from gp41 that overlap, or include all of, the residues in N36 or C34 can be effective inhibitors, at micromolar to nanomolar concentrations, of HIV infection and syncytia formation. Lu, M. et al., *Nature Struct. Biol.* 2:1075-1082 (1995); Jiang, S. et al., *Nature* 365:113 (1993); Wild, C. T. et al., *Proc. Natl. Acad. Sci., USA* 89:10537-10541 (1992); Wild, C. T. et al., *Proc. Natl. Acad. Sci. USA*, 91:9770-9774 (1994). Assessment previously of the inhibitory properties of the N51 and C43 peptides implied that these peptides work in a dominant negative manner (Herskowitz, I., *Nature* 329:219-222 (1987)) by binding to viral gp41 (Lu, M. et al., *Nature Struct. Biol.* 2:1075-1082 (1995)), a conclusion that was also reached through studies of a gp41 ectodomain chimeric protein (Chen, C. H. et al., *J. Virol.* 69:3771-3777 (1995)). Further evidence in support of a dominant-negative mechanism is provided by the finding that mutations in C-peptide derivatives that disrupt their interactions with N-peptide correlate with decreased potency as inhibitors. Wild, C. et al., *AIDS Res. Hum. Retroviruses* 11:323-325 (1995).

Figures 3A, 3B:
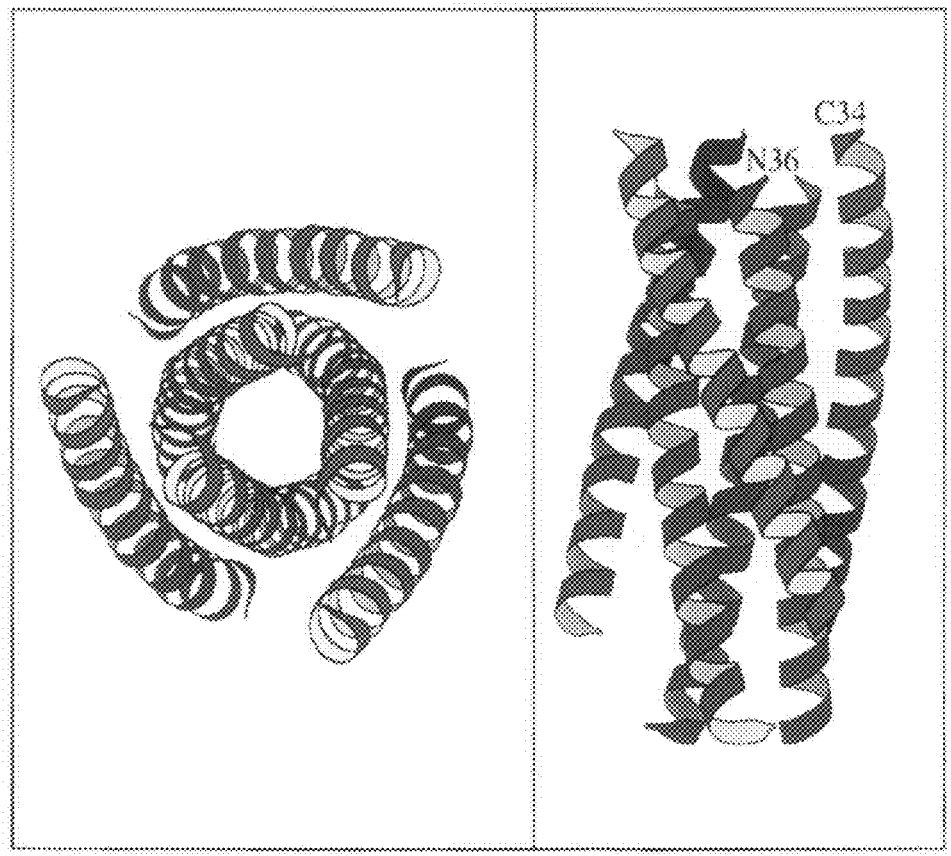
FIGS. 3A and 3B present overall views of the N36/C34 complex.
Figure 4:
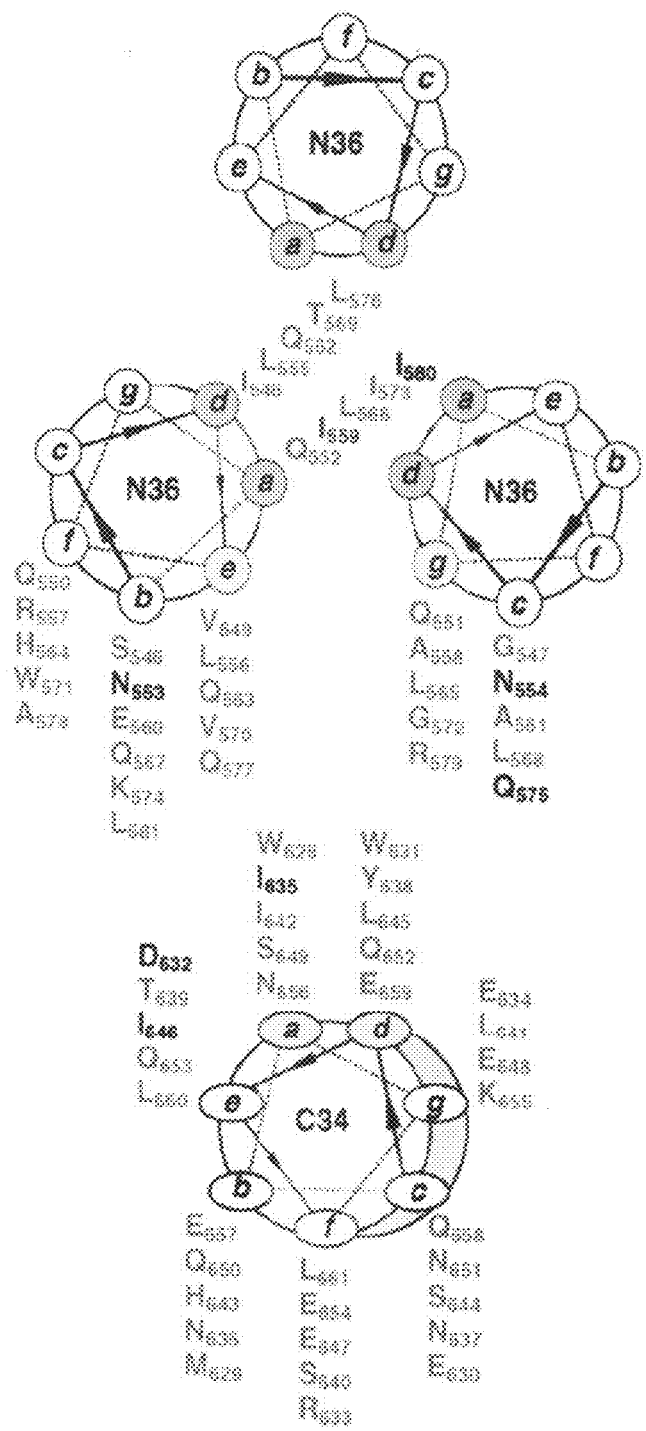
FIG. 4 shows a helical wheel representation of N36 and C34; three N36 helices and one C34 helix are represented as helical wheel projections. The view is from the top of the complex, as in FIG. 3A. The residues at each position are represented by the single-letter codes for amino acids. The N36 helices interact through "knobs-into-holes" packing interactions at the a and d positions. Positions of the N36 and C34 helices that occupy the interhelical space between two N36 helices and a C34 helix are shown (arrows). The helical wheel positions in C34 are indicated by ellipses to represent the oblique orientation of this helix relative to N36. At the top of the complex, C34 is slightly tilted towards the left N36 helix, while at the bottom of the complex, it is slightly tilted towards the right N36 helix.

The gp41 core crystal structure is fully consistent with this dominant-negative mechanism of inhibition (FIG. 3). The C-peptide derivatives could act as dominant-negative inhibitors by binding to the endogenous N-peptide coiled-coil trimer within viral gp41. The N-peptides might inhibit fusion by interfering with formation of the central, coiled-coil trimer within viral gp41, and/or by binding to endogenous viral C-peptide regions.

Both the N- and C-peptide classes of inhibitors are effective against a wide range of HIV strains, including laboratory-adapted strains and primary isolates. Wild, C. T. et al., *Proc. Natl. Acad. Sci., USA* 89:10537-10541 (1992); Jiang, S. et al., *Nature* 365:113 (1993); Wild, C. T. et al., *Proc. Natl. Acad. Sci., USA* 91:9770-9774 (1994). In contrast, soluble CD4 and many neutralizing antibodies are typically effective only on a limited subset of HIV strains (e.g., Daar, E. S. et al., *Proc. Natl. Acad. Sci., USA* 87:6574-6578 (1990); Palker, T. J. et al., *Proc. Natl. Acad. Sci., USA* 85:1932-1936 (1988); Nara, P. L. et al., *J. Virol.* 62:2622-2628 (1988); Moore, J. P. et al., *J Virology* 69:101-109 (1995). There is a striking conservation of residues involved in interactions between the N-peptide and C-peptide, comparing gp41 from HIV-1 and SIV. The broad neutralizing effects of the N- and C-peptides derive from the strong sequence conservation of these residues.

The highly conserved, deep cavities on the N-peptide coiled-coil trimer that accommodate conserved C-peptide residues are useful targets for the development of new peptidomimetic or small-molecule inhibitors of HIV infection. The two indole rings and neighboring sidechains that occupy the prominent cavity in N36 are a particularly attractive target for the design and/or development of new drugs or identification of existing drugs which inhibit HIV infection. Not only is this cavity deep and highly conserved, but two of the three key mutations that disrupt membrane fusion, discussed above, map to one wall of this cavity. Because some of the known potent peptide inhibitors (Wild, C. T. et al., *Proc. Natl. Acad. Sci., USA* 91:9770-9774 (1994)) extend beyond N36 and C34 and do not involve this cavity region, it is likely that other distinctive surface features exist in the interface between the N- and C-helices of longer peptides such as N51 and C43. Lu, M. et al., *Nature Struct. Biol.* 2:1075-1082 (1995). The importance of identifying drugs that target the HIV membrane-fusion machinery is emphasized by the success of combination drug regimens for the treatment of AIDS. As yet, these combination therapies do not target the HIV envelope. A method of identifying a drug which is an inhibitor of N36/C34 peptide interaction (and, thus, is an inhibitor of the HIV membrane fusion machinery and, as a result, reduces or prevents HIV entry into (infection of) cells is the subject of this invention. In the method, N36 and C34 are combined with a drug to be assessed, under conditions suitable for N36 and C34 to interact (suitable for cavities on the N-peptide coiled-coil trimer to accommodate C-peptide amino acid residues). The resulting combination is maintained under these conditions for sufficient time to permit N36 and C34 to interact (e.g., for sufficient time for N36 and C34 to interact in the absence of the drug being assessed). Whether interaction occurs and/or the extent to which N36 and, C34 interact is assessed, using known methods. If N36 and C34 do not interact or interact to a lesser extent in the presence of the drug being assessed than in the absence of the drug, the drug to be assessed is an inhibitor of N36/34 interaction. Such a drug is an inhibitor of the HIV membrane fusion machinery. Such an inhibitor can be further assessed, using in vitro or in vivo methods, for its ability to reduce or prevent HIV entry into cells.

Results of the work described have implications for gp41 function and viral membrane fusion. The structures of the cores of the membrane-fusion subunits from HIV, Mo-MLV and influenza virus are remarkably similar. It appears that these diverse viruses present fusion peptides to target cells via a common scaffold, in which the fusion peptides are atop a central, three-stranded coiled coil that is supported by additional, carboxy-terminal structures. This scaffold is likely to be a common feature of viral membrane-fusion proteins since many of these proteins contain coiled-coil signature sequences, with 4-3 heptad repeats of hydrophobic amino acids, adjacent to an amino-terminal fusion-peptide region. Delwart, E. L. et al., *AIDS Res. Hum. Retroviruses* 6:703-706 (1990); Chambers, P. et al., *J. Gen. Virol.* 71:3075-3080 (1990); Gallaher, W. R. et al., *AIDS Res. Hum. Retroviruses* 5:431-440 (1989). Moreover, studies of the fusion proteins of several paramyoviruses have identified regions with similarity to the N- and C-peptide regions of HIV and SIV gp41 (Lambert, D. M. et al., *Proc. Natl. Acad. Sci., USA* 93:2186-2191 (1996)). These common structural features suggest that the rich body of work investigating the mechanism of membrane fusion for many other viruses, including influenza, is relevant for understanding the mechanism of HIV-mediated membrane fusion.

Given the similarity in structure between the HIV gp41 core and the low-pH converted conformation of HA2, it is worth considering whether the structural rearrangements that occur during the transition of HA2 to the fusogenic state are analogous to those in gp41. In the native, non-fusogenic conformation of influenza HA, part of the N-terminal coiled-coil trimer seen in the fusogenic state (Bullough, P. A. et al., *Nature* 371:37-43 (1994)) is held in a non-helical, hairpin structure, as a result of extensive interactions with the receptor-binding HA1 subunit (Wilson, I. A. et al., *Nature* 289:366-373 (1981)). Thus, the receptor-binding HA1 subunit acts as a "clamp" that binds this N-terminal region of HA2, holding it in the non-coiled coil conformation. The receptor-binding domains dissociate in the fusogenic conformation of HA, as in HIV, although in the case of influenza, the HA1 subunits are still tethered via a disulfide bond to HA2. Upon release of the HA1 clamp, a dramatic conformational change in HA2 occurs, including coiled-coil formation by this N-terminal region (Bullough, P. A. et al., *Nature* 371:37-43 (1994); Carr, C. M. et al., *Cell* 73:823-832 (1993)).

A substantial conformational change in the envelope glycoprotein complex also appears to be critical during HIV infection, although few details are understood. It remains to be determined whether the HIV envelope complex also utilizes coiled-coil formation as part of a spring-loaded mechanism, or if the gp41 core structure determined here is present in the native as well as the fusogenic state. It is possible that the N36/C34 structure is the core structure of gp41 even when it is bound to gp120, and that release of gp120 simply exposes the fusion-peptide region of gp41. Alternatively, HIV gp120, like influenza HA1, may serve as a clamp that represses formation of the N36/C34 structure presented here, with gp120 shedding allowing its formation. This gp41 core structure serves as the starting point for addressing this and other essential structural questions about the mechanism of HIV entry into cells.

The present invention is illustrated by the following examples, which are not intended to be limiting in any way.

EXAMPLES

The materials and methods described below were used in the examples which follow.

Materials and Methods

Peptide Purification and Crystallization

Peptides N36 and C34 were synthesized by standard FMOC peptide chemistry and have an acetylated N-terminus and a C-terminal amide. N36 corresponds to residues 546 to 581 of gp160, while C34 corresponds to residues 628 to 661. After cleavage from the resin, the peptides were desalted on a Sephadex G-25 column (Pharmacia) and lyophilized. Peptides were then purified by reverse-phase high performance liquid chromatography (Waters, Inc.) on a Vydac C18 preparative column. The identity of the peptides was verified by mass spectrometry. Peptide concentration was determined by tyrosine and tryptophan absorbance in 6 M GuHCl. Edelhoch, H., *Biochemistry* 6:1948-1954 (1967).

To grow crystals, a 10 mg/ml stock of the N36/C34 complex was diluted 1:1 in a sitting drop with 80 mM $NH_4Cl$, 20% PEG200, and 50% isopropanol and allowed to equilibrate against a reservoir of 80 mM $NH_4Cl$, 20% PEG200, and 30% isopropanol. Crystals grew as hexagonal prisms and belonged to the space group P321 (a=b=49.5 Å, c=55.3 Å). For native data sets and heavy atom screens, crystals were flash-frozen in a MSC cryogenic crystal cooler (X-stream), and data was collected on a Rigaku RU-200 rotating-anode X-ray generator with an R-axis IIc detector.

Heavy Atom Screen and Phase Determination

Multiwavelength anomalous diffraction (MAD) data were collected at the Howard Hughes Medical Institute beamline X4A of the National Synchrotron Light Source at Brookhaven National Laboratory. Fluorescence spectra (1.1459 to 1.1354 Å) were obtained from a single flash-frozen crystal soaked in 0.04% $OsO_4$ in harvest buffer (80 mM $NH_4Cl$, 20% PEG200, 30% isopropanol) for 4 hours. Based on the fluorescence profile, individual data sets were collected on Fuji imaging plates at four wavelengths ($1_1$=1.1396 Å, $1_2$=1.1398 Å, $1_3$=1.1402 Å, and $1_4$=1.1344 Å). Reflections were integrated and scaled with DENZO and SCALEPACK. (Otwinowski, Z., *Daresbury Study Weekend Proceedings,* 1993.)

Data merging, phase determination and map generation were all performed using the CCP4 suite of programs. CCP4, *Acta Cryst.* D50:760-763 (1994). Anomalous and dispersive difference Patterson maps from MAD data sets all showed a single clear peak corresponding to the osmium binding site. The position of the site was calculated from the single z=0 Harker section and from cross peaks found at z=0.28 and z=0.71. Phases generated with the program MLPHARE (Otwinowski, Z., *Daresbury Study Weekend Proceedings,* 1991) gave an overall figure of merit of 0.89 (Table) and produced an interpretable electron density map with a clear solvent boundary. Density modification was subsequently performed using DM (Cowtan, K. D., *Newsletter on Protein Crystallography* 31:34-38 (1994)), resulting in maps of high quality in which electron density for the entire main chain and all side chains was evident.

Model Refinement

The polypeptide chain was traced and the side chains readily positioned into a 2.7 Å density-modified map using the program O (Jones, T. A., and Kjeldgaard, M., *O—The Manual*, Uppsala, Sweden: http://kaktus.kemi.aau.dk, 1992). The initial model of N36/C34 was refined with the program X-PLOR (Brünger, A. T., *A system for X-ray crystallography and NMR. X-PLOR Version* 3.1, Yale University Press, New Haven, Conn., 1992) against data to 2.0 Å from a native crystal. An anisotropic B-factor was applied to the native structure factors using XPLOR, and a free R set (Brünger, A. T., *Nature* 355:472-475 (1992)) was taken from the data prior to refinement (Table). The model was refined by iterative cycles of grouped B-factor, positional, and individual B-factor refinement. As the refinement proceeded, 43 waters were added and a bulk solvent correction was applied. At no time during the refinement did the molecule differ enough from the original model so as to require manual rebuilding, though main chain and side chain geometries were optimized in O between cycles of refinement. The quality of the structure was verified by PROCHECK (Laskowski, R. A. et al., *J. Appl. Cryst.* 26:283-291 (1993)), with all residues but one (Ile-580) occupying most-preferred regions of Ramachandran space. Ile-580 lies in the additionally allowed region of Ramachandran space and is the second residue from the C-terminus of the N36 peptide; inspection of the solvent-flattened MAD-phased maps confirmed its position.

Example 1

Production of Crystals of N36/C34

Figure 2:
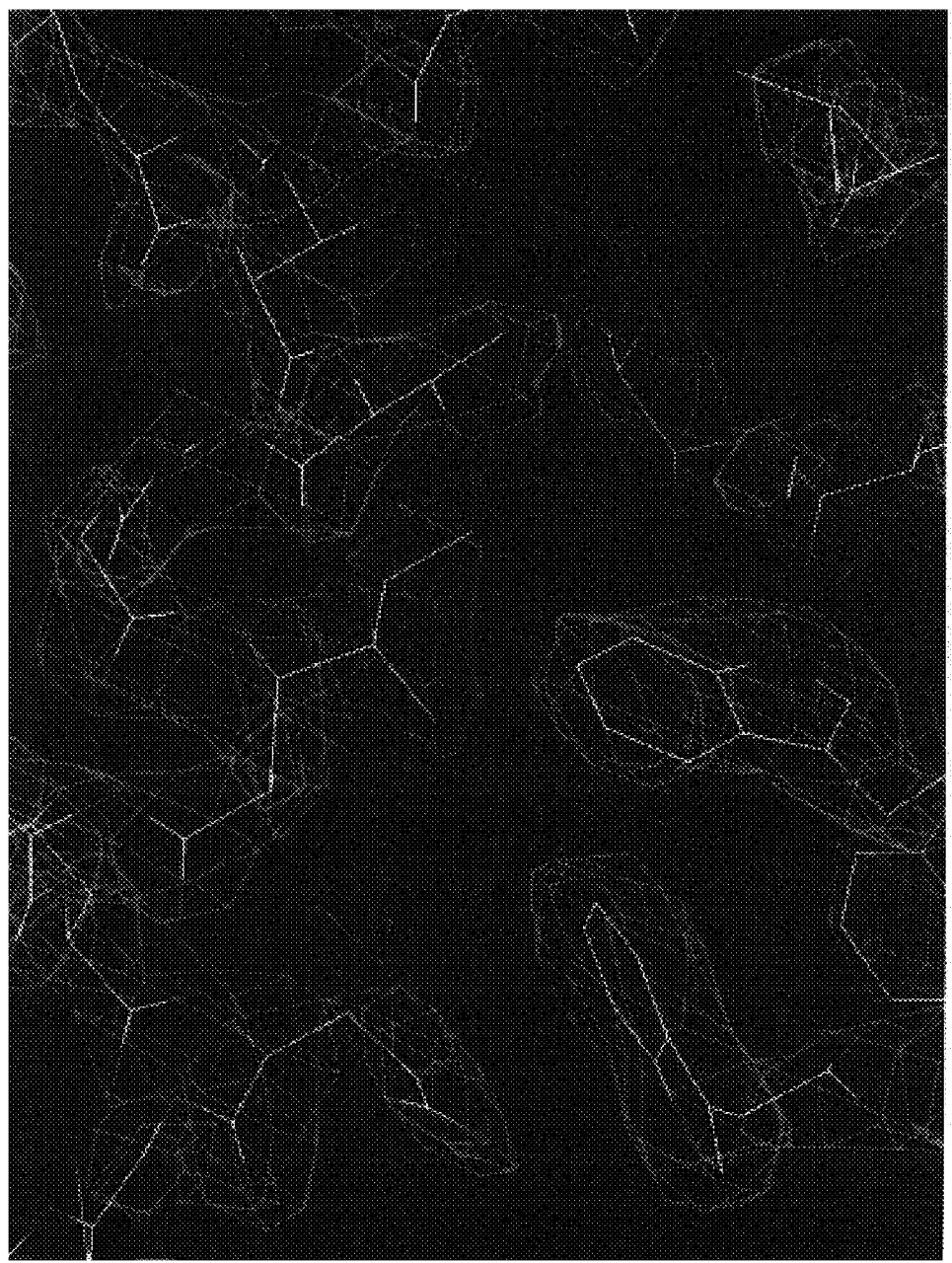
FIG. 2 is a representative portion of the initial electron density map calculated using experimental structure-factor amplitudes and solvent-flattened MAD phases, shown with the refined molecular model. The map is contoured at 1.5 standard deviations above the mean density. The figure was generated with the program O (Jones, T. A., and Kjeldgaard, M., *O—The Manual*, Uppsala, Sweden: http://kaktus.kemi-.aau.dk (1992)).

Crystals of N36/C34 were grown by sitting-drop vapor diffusion (see Methods). An initial model of the complex was built into an electron density map generated by multi-wavelength anomalous dispersion (MAD) analysis (Hendrickson, W. A., *Science* 254:51-58 (1991)) of an osmium-derivatized crystal. Details of data collection and MAD phasing statistics are listed in the Table. A representative portion of the solvent-flattened electron density map used for building the initial model is shown in FIG. 2. The structure was refined against data to 2.0 Å from a native crystal to yield an $R_{free}$ of 0.266 and an $R_{cryst}$ of 0.238 (Table).

TABLE

Crystallographic arid refinement statistics

Data collection

| Crystal | λ (Å) | % complete | $R_{sym}^1$ (%) | Resol. (Å) |
|---|---|---|---|---|
| Native | 1.5418 | 96.5 | 5.5 | 2.0 |
| OsO$_4$ λ1 | 1.1398 | 96.4 | 4.3 | 2.7 |
| OsO$_4$ λ2 | 1.1396 | 96.4 | 4.3 | 2.7 |
| OsO$_4$ λ3 | 1.1344 | 96.8 | 4.5 | 2.7 |
| OsO$_4$ λ4 | 1.1406 | 93.4 | 4.5 | 2.7 |

Phasing statistics (12-2.7 Å)

| Derivative | $R_{iso}^2$ (%) | $R_{diff}^3$ (%) (weight) | $R_{cullis}^4$ Acentric | $R_{cullis}^4$ Centric |
|---|---|---|---|---|
| OsO$_4$ λ1 vs. λ4 | 4.4 | 6.7 | 0.46 | 0.53 |
| OsO$_4$ λ2 vs. λ4 | 6.6 | 9.3 | 0.37 | 0.37 |
| OsO$_4$ λ2 vs. λ4 | 5.4 | 7.4 | 0.42 | 0.44 |
| OsO$_4$ λ3 vs. λ4 | | | | |

| Derivative | $R_{cullis}^4$ Anom. | Ph. power$^5$ Acentric | Ph. power$^5$ Centric | Occ.$^6$ | Anom. Occ.$^6$ |
|---|---|---|---|---|---|
| OsO$_4$ λ1 vs. λ4 | 0.21 | 2.46 | 1.53 | 0.075 | 2.165 |
| OsO$_4$ λ2 vs. λ4 | 0.22 | 3.34 | 2.36 | 0.132 | 1.784 |
| OsO$_4$ λ3 vs. λ4 | 0.35 | 2.94 | 2.12 | 0.105 | 1.005 |

Overall FIGURE of merit (before solvent flattening): 0.89

Refinement statistics (12-2.0 Å)

| Non-hydrogen protein atoms | Waters | Number of reflections working | free | $R_{cryst}^7$ | $R_{free}^7$ | R.m.s. deviations bonds (Å) | angles (°) |
|---|---|---|---|---|---|---|---|
| 596 | 43 | 5212 | 371 (7.12%) | 0.238 | 0.266 | 0.014 | 2.742 |

$^1R_{sym} = \Sigma\Sigma j||j-<|>|/\Sigma|<|>|$, where |j is the recorded intensity of the reflection | and <|> is the mean recorded intensity over multiple recordings.
$^2R_{iso} = \Sigma||F_{\lambda i} \pm F_{\lambda 4}| - |F_{\lambda i}||/\Sigma|F_{\lambda 4}|$, where $F_{\lambda i}$ is the structure factor at wavelength λi and $F_{\lambda 4}$ is the structure factor at the reference wavelenth λ4.
$^3R_{diff} = [\Sigma|(F^2_{(\lambda 4)} - \Phi_{mean})/\phi F^2_{(\lambda 4)}| + |(F^2_{(\lambda i)} - \Phi_{mean})/\phi F^2_{(\lambda i)}|]/[\Sigma[(F^2_{(\lambda 4)}/\phi F^2_{(\lambda 4)}) + (F^2_{(\lambda i)}/\phi F^2_{(\lambda i)})]]$, where $\Phi_{mean} = [(F^2_{(\lambda 4)}/\phi F^2_{(\lambda 4)}) + (F^2_{(\lambda i)}/\phi F^2_{(\lambda i)})]/[(1/\phi F^2_{(\lambda 4)}) + (1/\phi F^2_{(\lambda i)})]$ and $\phi F^2_{(n)} = [\text{Variance }(F^2_{(n)})]4F^2_{(n)}$.
$^4R_{cullis} = \Sigma||F_{\lambda i} \pm F_{\lambda 4}| - |F_{h(\lambda i),c}||/\Sigma|F_{\lambda i} \pm F_{\lambda 4}|$, where $F_{h(\lambda i),c}$ is the calculated heavy atom structure factor.
$^5$Phase power = $<F_{h(\lambda i)}>/E$, where $<F_{h(\lambda i)}>$ is the root-mean-square heavy atom structure factor and E is the residual lack of closure error.
$^6$Occupancies are values output from MLPHARE.
$^7R_{cryst, free} = \Sigma||F_{obs}| - |F_{calc}||/|F_{obs}|$, where the crystallographic and free R factors are calculated using the working and free reflection sets, respectively.

Example 2

Assessment of the Structure of the N36/C34 Complex

The N36/C34 complex is a six-stranded helical bundle (FIG. 3). The center of this bundle consists of a parallel, trimeric coiled coil of three N36 helices wrapped in a gradual left-handed superhelix. Three C34 helices wrap antiparallel to the N36 helices in a left-handed direction around the outside of the central coiled-coil trimer. The complex is a cylinder measuring ~35 Å in diameter and ~55 Å in height.

As in other naturally-occurring coiled coils (Cohen, C. et al., *Proteins* 7: 1-15 (1990)), the interior residues at the a and d positions of the N36 heptad repeat are predominantly hydrophobic, although occasional buried polar interactions are also present in the central three-stranded coiled coil (FIG. 4). A sequence comparison of HIV-1 (HXB2 strain) and SIV (Mac239 strain) gp41 shows that the residues at these two heptad-repeat positions are highly conserved (FIG. 4). The characteristic "knobs-into-holes" packing of coiled coils is utilized, whereby the residues (knobs) at the a and d layers pack into cavities (holes) between four residues of an adjacent helix (Crick, F. H. C., *Acta Cryst.* 6:689-697 (1953); O'Shea, E. K. et al., *Science* 254:539-544 (1991)). Of the three types of knobs-into-holes packing geometry observed in coiled-coil structures (Harbury, P. B. et al., *Science* 262:1401-1407 (1993); Harbury, P. et al., *Nature* 371:80-83 (1994)), the N36 trimer demonstrates exclusively "acute" packing geometry, similar to that found in the crystal structure of an isoleucine-zipper trimer (Harbury, P. et al., Nature 371:80-83 (1994)). This type of packing arrangement in the interior of the coiled coil is characteristic of trimers because it allows β branched residues (e.g., isoleucine) to pack favorably at both the a and d positions (Harbury, P. et al., Nature 371:80-83 (1994)). Trimeric coiled coils, like the N36 trimer (FIG. 4), tend to have β branched residues at both the a and d positions.

Although complexes of the N- and C-peptides are clearly trimeric (Lu, M. et al., Nature Struct. Biol. 2:1075-1082 (1995); Blacklow, S. C. et al., Biochemistry 34:14955-14962 (1995)), isolated N-peptides corresponding to the 4-3 hydrophobic repeat from gp41 have been reported to form tetramers, leading to conflicting conclusions regarding the oligomeric state of gp41 (Lawless, M. et al., Biochemistry 35:13697-13708 (1996); Rabenstein, M. et al., Biochemistry 34:13390-13397 (1995); Rabenstein, M. D. et al., Biochemistry 35:13922-13928 (1996); Shugars, D. C. et al., J. Virol. 70:2982-2991 (1996)). An electrostatic potential map of the N36 coiled-coil trimer shows that its surface is largely uncharged. The grooves that are the sites for C34 interaction are lined with predominantly hydrophobic residues (see below) that would be expected to lead to aggregation upon exposure to solvent. Indeed, previous studies have shown that the isolated N-peptides tend to aggregate (Blacklow, S. C. et al., Biochemistry 34:14955-14962 (1995); Lu, M. et al., Nature Struct. Biol. 2:1075-1082 (1995)). Thus, conclusions regarding the oligomerization state of gp41 based on studies of isolated N-peptides are probably misleading. The N36/C34 complex shows a much more highly charged surface due to acidic residues on the outside of the C34 helices, explaining the greater solubility of the heterodimeric complex.

Example 3

Determination of Interactions Between the—and C-Peptide Helices

Three C34 helices pack obliquely against the outside of the N36 coiled-coil trimer in an antiparallel orientation. These C34 helices interact with N36 mainly through hydrophobic residues in three grooves on the surface of the central coiled-coil trimer. Sequence comparisons between HIV and SIV gp41 shows that the residues lining these grooves are highly conserved. In contrast, the N36 residues flanking the C34 helices are divergent between HIV and SIV.

This pattern of sequence conservation is also apparent on a helical wheel representation of three N36 helices and one C34 helix (FIG. 4). In this diagram, the residue positions in C34 are depicted as ellipses to indicate the oblique tilt of the C34 helix relative to the N36 superhelix and to emphasize that C34 is not part of a coiled coil. Residues at the e and g positions of the N36 helices lie on the outside of the central coiled coil and point into the triangular interhelical space between two N36 helices and a buttressing C34 helix. In general, residues at positions a and d of C34 pack against residues at the e and g positions of the N36 helices (FIG. 4), although contacts at other positions are often observed. Comparing HIV and SIV gp41, no nonconservative changes exist at the e and g positions of the N36 helix, and only two such changes occur at the a and d positions of C34. In contrast, 8 of the 9 nonconservative changes in the N36 helix occur at the outside f, b, and c positions, while 13 of the 15 nonconservative changes in the C34 helix occur at positions other than a and d. The sequence of the N-peptide region of gp41 is among the most highly conserved within the HIV envelope glycoprotein. Our results show that the high sequence conservation in this region results from selective pressure on the e and g positions to retain C34 peptide interactions, as well as pressure on the a and d positions to maintain trimeric coiled-coil interactions.

Each of the grooves on the surface of the N36 trimer has a particularly deep cavity. This cavity is large (~16 Å long, ~7 Å wide, and 5-6 Å deep) and accommodates three hydrophobic residues from the abutting C34 helix: Ile-635, Trp-631 and Trp-628. The top of the cavity is lined by Leu-566 of the left N36 helix and Leu-565 of the right N36 helix. Side chains from the left N36 helix form the left side of the cavity, including residues (top to bottom) Val-570, Lys-574 (aliphatic portion), and Gln-577. The right wall is formed by residues Leu-568, Trp-571, and Gly-572 of the right N36 helix. The floor of the cavity is composed of Thr-569 and Leu-576 of the right N36 helix, and also Ile-573 of both N36 helices. With the exception of Ile-573 (which is replaced by Thr), all the residues forming the cavity are identical between HIV-1 and SIV. In addition to these predominately hydrophobic interactions within the cavity, Asp-632 of C34 forms a conserved salt bridge with Lys-574 of N36 immediately to the left of the cavity.

Example 4

Comparison of the Structure of the N36/C34 Complex with the low-pH Induced Conformation of HA The N36/C34 complex shows striking structural similarity to the low-pH induced conformation of the influenza $HA_2$ subunit ($TBHA_2$) (Bullough, P. A. et al., Nature 371:37-43 (1994)) and to the TM subunit of Mo-MLV (Fass, D. et al., Nature Struct. Biol. 3:465-469 (1996)), each of which has been proposed to be a fusogenic conformation. Remarkably, the core of each of the three structures contains a three-stranded coiled coil that would be adjacent to the amino-terminal fusion peptide. The trimeric coiled coil of gp41 is very similar to that of the Mo-MLV TM, both having a similar superhelical pitch (~175 Å) and a regular 4-3 periodicity. In contrast, the $TBHA_2$ coiled coil is atypical because it contains two regions with skips in the 4-3 periodicity, resulting in an underwound superhelix (pitch of 300-400 Å). As in the gp41 core structure, $TBHA_2$ contains three antiparallel helices that are packed, with a left-handed tilt, against the central trimeric coiled coil.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of identifying an antibody that inhibits the HIV membrane fusion machinery by inhibiting interactions between the N36 peptide trimer and the C34 peptide trimer of HIV gp41, comprising:
   (a) combining HIV gp41 N36 peptide trimer, HIVgp41 C34 peptide trimer and an antibody to be assessed for its ability to inhibit interaction between the two trimers, to produce a combination;
   (b) maintaining the combination under conditions appropriate for interactions to occur between N36 peptide trimers and C34 peptide trimers; and
   (c) assessing whether interactions occurred between N36 peptide trimers and C34 peptide trimers,
   wherein if interactions between the N36 peptide trimer and the C34 peptide trimer did not occur in the presence of the antibody or occurred to a lesser extent in the presence of the antibody than in its absence, the antibody is an antibody that inhibits the HIV membrane fusion machinery.

2. The method of claim 1 wherein in step (c) the interaction assessed is packing of amino acid residues or peptides of C34 peptide trimers into highly conserved cavities on N36 peptide trimers.

3. The method of claim 2 wherein the interaction assessed is packing of amino acid residues or peptides of C34 into cavities on N36 peptide trimers which are:
   (a) lined by Leu-566 of the left N36 helix and Leu-565 of the right N36 helix ;
   (b) formed on the left side by sidechains from the left N36 helix, including residue (top to bottom) Val-570, Lys-574 (aliphatic portion) and Gln-577;
   (c) formed on the right side by residues Leu-568, Trp-571 and Gly-572 of the right N36 helix; and
   (d) composed on its floor of Thr-569, Ile-573 and Leu-576, wherein amino acid numbers refer to the positions as indicated in FIG. 1.

* * * * *

UNITED STATES PATENT AND TRADEMARK OFFICE
CERTIFICATE OF CORRECTION

PATENT NO. : 7,402,396 B2 Page 1 of 1
APPLICATION NO. : 10/680853
DATED : July 22, 2008
INVENTOR(S) : David C. Chan et al.

It is certified that error appears in the above-identified patent and that said Letters Patent is hereby corrected as shown below:

<u>Column 20</u>
Line 49, delete "lle-573" and insert --Ile-573--.

Signed and Sealed this

Sixteenth Day of December, 2008

JON W. DUDAS
*Director of the United States Patent and Trademark Office*